US009006407B2

(12) United States Patent
Klink et al.

(10) Patent No.: US 9,006,407 B2
(45) Date of Patent: *Apr. 14, 2015

(54) THERAPEUTIC RIBONUCLEASES

(71) Applicant: Quintessence Biosciences, Inc., Madison, WI (US)

(72) Inventors: Tony Klink, Madison, WI (US); John Kink, Madison, WI (US); Laura Strong, Stoughton, WI (US)

(73) Assignee: Quintessence Biosciences, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/149,491

(22) Filed: Jan. 7, 2014

(65) Prior Publication Data
US 2014/0128457 A1 May 8, 2014

Related U.S. Application Data

(63) Continuation of application No. 13/545,387, filed on Jul. 10, 2012, now Pat. No. 8,628,768, which is a continuation of application No. 13/231,050, filed on Sep. 13, 2011, now Pat. No. 8,216,567, which is a continuation of application No. 12/572,016, filed on Oct. 1, 2009, now Pat. No. 8,029,782.

(60) Provisional application No. 61/101,905, filed on Oct. 1, 2008.

(51) Int. Cl.
*C12N 9/22* (2006.01)
*A61K 38/46* (2006.01)
*A61K 38/00* (2006.01)

(52) U.S. Cl.
CPC ............... *A61K 38/465* (2013.01); *C12N 9/22* (2013.01); *A61K 38/00* (2013.01); *C12Y 301/2601* (2013.01)

(58) Field of Classification Search
CPC ... C12N 9/22; A61K 38/465; C12Y 301/2601
USPC .......................................... 424/94.6; 435/199
See application file for complete search history.

(56) References Cited

U.S. PATENT DOCUMENTS

| | | |
|---|---|---|
| 4,424,311 A | 1/1984 | Nagaoka |
| 4,708,930 A | 11/1987 | Kortright |
| 4,743,543 A | 5/1988 | Kortright |
| 4,892,935 A | 1/1990 | Yoshida |
| 4,914,021 A | 4/1990 | Toth |
| 4,918,164 A | 4/1990 | Hellstrom |
| 4,921,789 A | 5/1990 | Salem |
| 4,921,790 A | 5/1990 | O'brien |
| 4,939,240 A | 7/1990 | Chu |
| 4,963,484 A | 10/1990 | Kufe |
| 5,053,489 A | 10/1991 | Kufe |
| 5,096,815 A | 3/1992 | Ladner et al. |
| 5,110,911 A | 5/1992 | Samuel |
| 5,198,346 A | 3/1993 | Ladner et al. |
| 5,200,182 A | 4/1993 | Kiczka |
| 5,223,409 A | 6/1993 | Ladner et al. |
| 5,270,163 A | 12/1993 | Gold |
| 5,270,204 A | 12/1993 | Vallee et al. |
| 5,286,487 A | 2/1994 | Vallee et al. |
| 5,286,637 A | 2/1994 | Veronese et al. |
| 5,359,030 A | 10/1994 | Ekwuribe |
| 5,389,537 A | 2/1995 | Raines et al. |
| 5,446,090 A | 8/1995 | Harris |
| 5,475,096 A | 12/1995 | Gold |
| 5,512,443 A | 4/1996 | Schlom |
| 5,545,530 A | 8/1996 | Satomura |
| 5,559,212 A | 9/1996 | Ardelt |
| 5,562,907 A | 10/1996 | Arnon |
| 5,660,827 A | 8/1997 | Thorpe et al. |
| 5,672,662 A | 9/1997 | Harris et al. |
| 5,693,763 A | 12/1997 | Codington |
| 5,733,731 A | 3/1998 | Schatz et al. |
| 5,739,208 A | 4/1998 | Harris |
| 5,786,457 A | 7/1998 | Nett et al. |
| 5,808,005 A | 9/1998 | Codington |
| 5,811,238 A | 9/1998 | Stemmer et al. |
| 5,824,544 A | 10/1998 | Armentano et al. |
| 5,824,784 A | 10/1998 | Kinstler |
| 5,830,721 A | 11/1998 | Stemmer et al. |
| 5,830,730 A | 11/1998 | German et al. |
| 5,837,458 A | 11/1998 | Minshull et al. |
| 5,840,296 A | 11/1998 | Raines et al. |
| 5,840,840 A | 11/1998 | Rybak et al. |
| 5,855,866 A | 1/1999 | Thorpe |

(Continued)

FOREIGN PATENT DOCUMENTS

| | | |
|---|---|---|
| CN | 101268186 | 9/2008 |
| EP | 1316318 | 6/2003 |

(Continued)

OTHER PUBLICATIONS

Pous J., et al, "Three-dimensional structure of human RNase 1 AN7 at 1.9 A resolution," Acta Crystallogr D Biol Crystallogr., (2001) 57, pp. 498-505.
Press et al., "Expression of the HER-2/neu proto-oncogene in normal human adult and fetal tissues," 1990 Oncogene 5:953-62.
Psarras, K, et al., "Human pancreatic RNase1-human epidermal growth factor fusion: An entirely human immunotoxin analog with cytotoxic properties against squamous cell carcinomas," Protein Eng, 1998, 11:1285-92.
Raines, R.T., et al., "A New Remote Subsite in Ribonuclease A," J. Biol. Chem, 273, pp. 34134-34138 (1998).
Reddi, KK., "Nature and Origin of Human Serum Ribonuclease" Biochem. Biophys. Res. Commun. 1975, 67(1), pp. 110-118.
Ribo, M., et al., "Heterogeneity in the Glycosylation Pattern of Human Pancreatic Ribonuclease," Biol. Chem. Hoppe-seyler, 375, pp. 357-363 (1994).

(Continued)

*Primary Examiner* — Tekchand Saidha
(74) *Attorney, Agent, or Firm* — David A. Casimir; Casimir Jones, S.C.

(57) ABSTRACT

The present invention relates to the use of ribonucleases (RNases) in the treatment or prevention of disease.

10 Claims, No Drawings

(56) References Cited

U.S. PATENT DOCUMENTS

| | | |
|---|---|---|
| 5,866,119 A | 2/1999 | Bandman et al. |
| 5,872,154 A | 2/1999 | Wilson et al. |
| 5,885,808 A | 3/1999 | Spooner et al. |
| 5,892,019 A | 4/1999 | Schlom |
| 5,892,020 A | 4/1999 | Mezes |
| 5,900,461 A | 5/1999 | Harris |
| 5,932,462 A | 8/1999 | Harris |
| 5,955,073 A | 9/1999 | Rybak et al. |
| 5,981,225 A | 11/1999 | Kochanek et al. |
| 5,990,237 A | 11/1999 | Bentley |
| 5,994,106 A | 11/1999 | Kovesdi et al. |
| 5,994,128 A | 11/1999 | Fallaux et al. |
| 5,994,132 A | 11/1999 | Chamberlain et al. |
| 6,001,557 A | 12/1999 | Wilson et al. |
| 6,019,978 A | 2/2000 | Ertl et al. |
| 6,033,908 A | 3/2000 | Bout et al. |
| 6,045,793 A | 4/2000 | Rybak et al. |
| 6,051,230 A | 4/2000 | Thorpe et al. |
| 6,077,499 A | 6/2000 | Griffiths et al. |
| 6,083,477 A | 7/2000 | Goldenberg |
| 6,183,744 B1 | 2/2001 | Goldenberg |
| 6,197,528 B1 | 3/2001 | Wu et al. |
| 6,214,966 B1 | 4/2001 | Harris |
| 6,271,369 B1 | 8/2001 | Torrence et al. |
| 6,280,991 B1 | 8/2001 | Raines |
| 6,312,694 B1 | 11/2001 | Thorpe et al. |
| 6,348,558 B1 | 2/2002 | Harris |
| 6,362,254 B2 | 3/2002 | Harris |
| 6,362,276 B1 | 3/2002 | Harris |
| 6,395,276 B1 | 5/2002 | Rybak et al. |
| 6,399,068 B1 | 6/2002 | Goldenberg |
| 6,406,897 B1 | 6/2002 | Kim et al. |
| 6,416,758 B1 | 7/2002 | Thorpe et al. |
| 6,428,785 B1 | 8/2002 | Gokcen |
| 6,432,397 B1 | 8/2002 | Harris |
| 6,437,025 B1 | 8/2002 | Harris |
| 6,448,369 B1 | 9/2002 | Bentley |
| 6,515,100 B2 | 2/2003 | Harris |
| 6,541,543 B2 | 4/2003 | Harris |
| 6,541,619 B1 | 4/2003 | Park et al. |
| 6,610,281 B2 | 8/2003 | Harris |
| 6,649,383 B1 | 11/2003 | Cheung |
| 6,649,393 B1 | 11/2003 | Youle et al. |
| 6,653,104 B2 | 11/2003 | Goldenberg |
| 6,664,331 B2 | 12/2003 | Harris |
| 6,676,941 B2 | 1/2004 | Thorpe et al. |
| 6,737,505 B2 | 5/2004 | Bentley |
| 6,828,401 B2 | 12/2004 | Nho |
| 6,838,076 B2 | 1/2005 | Patton |
| 6,864,327 B2 | 3/2005 | Bentley |
| 6,864,350 B2 | 3/2005 | Harris |
| 6,894,025 B2 | 5/2005 | Harris |
| 6,962,702 B2 | 11/2005 | Hansen et al. |
| 7,033,572 B2 | 4/2006 | Goldenberg |
| 7,125,541 B2 | 10/2006 | Thorpe et al. |
| 7,199,223 B2 | 4/2007 | Bossard |
| 7,355,019 B2 | 4/2008 | Backer et al. |
| 7,416,875 B2 | 8/2008 | Raines et al. |
| 7,476,725 B2 | 1/2009 | Zaplisky |
| 8,003,111 B2 | 8/2011 | Chang et al. |
| 8,029,782 B2 | 10/2011 | Klink et al. |
| 8,216,567 B2 | 7/2012 | Klink et al. |
| 2001/0049434 A1 | 12/2001 | Conklin et al. |
| 2002/0006379 A1 | 1/2002 | Hansen et al. |
| 2002/0037289 A1 | 3/2002 | Thorpe et al. |
| 2002/0048550 A1 | 4/2002 | Vallera et al. |
| 2002/0106359 A1 | 8/2002 | Gokcen |
| 2002/0119153 A1 | 8/2002 | Thorpe et al. |
| 2002/0187153 A1 | 12/2002 | Goldenberg |
| 2003/0031669 A1 | 2/2003 | Goldenberg |
| 2003/0114368 A1 | 6/2003 | Rybak |
| 2003/0219785 A1 | 11/2003 | Hallahan et al. |
| 2005/0158273 A1 | 7/2005 | Harris |
| 2005/0181449 A1 | 8/2005 | Kozlowski |
| 2005/0261232 A1 | 11/2005 | Strong et al. |
| 2005/0287113 A1 | 12/2005 | Zaplisky |
| 2006/0292137 A1 | 12/2006 | Raines et al. |
| 2007/0166278 A1 | 7/2007 | Veronese |
| 2008/0025964 A1 | 1/2008 | Kink |
| 2008/0095755 A1 | 4/2008 | Kink |

FOREIGN PATENT DOCUMENTS

| | | |
|---|---|---|
| JP | 2003-206236 | 7/2003 |
| WO | 9101758 | 2/1991 |
| WO | 96/21469 | 7/1996 |
| WO | 97/38134 | 10/1997 |
| WO | 98/33941 | 8/1998 |
| WO | 99/02685 | 1/1999 |
| WO | 99/07724 | 2/1999 |
| WO | 00/09675 | 2/2000 |
| WO | 00/12738 | 3/2000 |
| WO | 00/31242 | 6/2000 |
| WO | 01/94547 | 12/2001 |
| WO | 02/25630 | 1/2002 |
| WO | 03/031581 | 4/2003 |
| WO | 2006/138558 A1 | 12/2006 |
| WO | 2007/149594 | 12/2007 |
| WO | 2008/010991 A1 | 1/2008 |

OTHER PUBLICATIONS

Roberts B., et al., "Directed evolution of a protein: Selection of potent . . . " Proc. Natl. Acad. Sci., (1992) 89, pp. 2429-2433.

Roberts et al. "Chemistry for peptide and protein PEGylation," 2002 Advanced Drug Delivery Reviews 54:459-476.

Roehrl et al., "A General Framework for Development and Data Analysis of Competitive High-Throughput Screens for Small-Molecule Inhibitors of Protein-Protein Interactions by Fluorescence Polarization," 2004 Biochem 43: 16056-16066.

Rosenberg H F et al., "Eosinophils, Eosinophil Ribonucleases, and their Role in Host Defense Against Respiratory Virus Pathogens," 2001, J Leukocyte Bio, Fed Am Soc Exper Bio, 70, pp. 691-698.

Rosenberg H, et al, "Molecular cloning and characterization of a novel human ribonuclease (RNase k6): increasing diversity in the enlarging ribonuclease gene family," Nucleic Acids Research, (1994) 24, pp. 3507-3513.

Rybak S., et al., "Rational Immunotherapy With Ribonuclease Chimeras," Cell Biophysics, (1992) 21(1-3), pp. 121-138.

Rybak, S., et al., "Cytotoxic Potential of Ribonuclease and Ribonuclease Hybrid Proteins," Journal of Biological Chemistry, (1991) 266(31), pp. 21202-21207.

Scott J., et al., "Searching for peptide ligands with an Epitope library," Science, (1990) 249, pp. 386-390.

Shapiro, R., et al., "Analysis of the Interactions of Human Ribonuclease Inhibitor with Angiogenin and Ribonuclease A by Mutagenesis: Importance of Inhibitor Residues Inside versus Outside the C-terminal "Hot Spot"," J. Mol. Biol., 302, pp. 497-519 (2000).

Skerra, et al., "Engineered protein scaffolds for molecular recognition," J Mol Recognit. 2000, 13:167-87.

Smith G., "The progeny of sexual PCR," Nature, (1994) 370, pp. 324-325.

Smith et al., "Potent Inhibition of Ribonuclease A by Oligo(vinylsulfonic Acid)", 2003 J Biol Chem 278:20934-30938.

Sorrentino and Glitz, "Ribonuclease activity and substrate preference of human eosinophil cationic protein (ECP)" 1991 FEBS Lett. 288:23-6.

Sorrentino, S., et al., "Degradation of Double-Stranded RNA by Human Pancreatic Ribonuclease: Crucial Role of Noncatalytic BasicAmino Acid Residues," Biochemistry 42, pp. 10182-10190 (2003).

Springer, et al., "Blood group Tn-active macromolecules from human carcinomas and erythrocytes: characterization of and specific reactivity with mono- and poly-clonal anti-Tn antibodies induced by various immunogens," 1988 Carbohydr Res 178:271-292.

Stemmer W., "DNA shuffling by random fragmentation and reassembly . . . ," Proc. Natl. Acad. Sci., (1994) 91, pp. 10747-10751.

Stemmer W., "Rapid evolution of a protein in vitro by DNA shuffling," Nature, (1994) 370, pp. 389-391.

(56) References Cited

OTHER PUBLICATIONS

Strong, L E et al., "408 Poster Human RNase 1 variants are effective anti-cancer agents," 2006, EP J Cancer Supp, Pergamon, Oxford, GB, 4, p. 125.

Strong, Laura E, et al., "Human ribonuclease variants with broad anti-cancer activity," 2006, Am Assoc for Cancer Res Annual Mtg, 47, P514.

Stryer L., "Introduction of Proteins," Biochemistry, 2nd Edition,(1981) pp. 17-21.

Suzuki M., et al., "Engineering receptor-mediated cytotoxicity into human ribonucleases . . . ," Nature Biotechnology, (1999) 17, pp. 265-270.

Swaminathan G., et al, "Atomic Resolution (0.98 A) Structure of Eosinophil-Derived Neurotoxin," Biochemistry, (2002) 41, pp. 3341-3352.

Terzyan S.S., "The Three-dimensional Structure of Human RNase 4, Unliganded and Complexed with d(Up), Reveals the Basis for its Uridine Selectivity", et al, J Mol. Biol., (1999) 285, pp. 205-214.

Tjandra, et al., "Application of mammary serum antigen assay in the management of breast cancer: A preliminary report," 1988 J Surg 75:811-817.

Tortora et al., "Synergistic Inhibition of Growth and Induction of Apoptosis by 8-Chloro-cAMP and Paclitaxel or Cisplatin in n. Human Cancer Cells," 1997 Cancer Res 57:5107-5111. X.

Trautwein, K. et al., "Site-directed mutagenesis of bovine pancreatic ribonuclease: lysine-41 and aspartate-121," FEBS Lett., 281, pp. 275-277 (1991).

Tuerk et al., "In vitro evolution of functional nucleic acids : high-affinity RNA ligands of HIV-1 proteins," 1993 Gene 137:33-9.

Tortora et al., "Synergistic Inhibition of Growth and Induction of Apoptosis by 8-Chloro-cAMP and Paclitaxel or Cisplatin in Human Cancer Cells," 1997 Cancer Res 57:5107-5111. X.

Vasey et al., "Phase I Clinical and Pharmacokinetic Study of PK1 [N-(2-Hydroxypropyl) methacrylamide Copolymer Doxorubicin] . . . ," 1999 Clin Cancer Res 5:83-94.

Veronese I "Surface Modification of Proteins" Applied Biochemistry and Biotechnology, vol. 11, 1985, pp. 141-152.

Veronese II "Peptide and protein PEGylation: a review of problems and solutions" Biomaterials 22 (2001) 405-417.

Wang, "An exact mathematical expression for describing competitive binding of two different ligands to a protein molecule", 1995 FEBS Lett 360: 111-114.

Yamamura, t., et al., "Immunosuppressive and Anticancer Effect of a Mammalian Ribonuclease that Targets High-affinity Interleukin-2 receptors," European Journal of Surgery, (2002) 168(1), pp. 49-54.

Zaffaroni et al., "Induction of apoptosis by taxol and cisplatin and effect on cell cycle-related proteins in cisplatin-sensitive and -resistant human ovarian cancer cells," 1998 Brit. J. Cancer 77:1378-1385.

Zalipsky, "Functionalized Poly(ethylene glycol) for Preparation of Biologically Relevant Conjugates," Bioconjugate Chem 6, 150-165 (1995).

Zhang J., et al, "Human RNase 7: a new cationic ribonuclease of the RNase A superfamily," Nucleic Acids Res., (2003) 31, pp. 602-607.

Zhang J., et al, "RNase 8, A Novel RNase A Superfamily Ribonuclease Expressed Uniquely in Placenta," Nucleic Acids Res., (2002) 30, pp. 1169-1175.

Zhang J., et al., "Directed evolution of a fucosidase from a galatosidase by DNA shuffling and screening," Proc. Natl. Acad. Sci., (1997) 94, pp. 4504-4509.

Zhao H., et al., "Optimization of DNA shuffling for high fidelity recombination," Nucleic Acids Research,(1997) 25(6), pp. 1307-1308.

Zhou, et al., "Selection of Antibiotic-Resistant Bacterial Mutants: Allelic Diversity among Fluoroquinolone-Resistant Mutations," 2000 JID 182:517-525.

Jinno H., et al., "Epidermal Growth Factor Receptor-Dependent Cytotoxicity for Human Squamous Carcinoma Cell Lines . . . ," Life Sciences, (1996) 58(21), pp. 1901-1908.

Jinno U.H., et al., "Epidermal growth factor receptor-dependent cytotoxic effect by an EGF-ribonuclease conjugate . . . " Cancer Chemotherapy and Pharmacology, (1996) 38(4), pp. 303-308.

Kelemen et al., "Hypersensitive substrate for ribonucleases", 1999 Nucl Acids Res, 27: 3696-3701.

Kinstler et al., "Mono-N-terminal poly(ethylene glycol)-protein conjugates," 2002 Advanced Drug Delivery Reviews 54:477-485.

Kirpotin et al., "Sterically Stabilized Anti-HER2 Immunoliposomes: Design and Targeting to Human Breast Cancer Cells in Vitro," 1997 Biochem 36:66.

Kjeldsen et al., "Preparation and Characterization of Monoclonal Antibodies Directed to the Tumor-associated O-linked Sialosy 1-2 . . . ," 1988 Cancer Res 48:2214-2220.

Klink ,T A, et al., "Conformational stability is a determinant of ribonuclease A cytotoxicity," 2000, J Biolog Chem, 275:17463-17467.

Kobe, et al., "Mechanism of ribonuclease inhibition by ribonuclease inhibitor protein based on the crystal structure of its complex with ribonuclease A," J Mol Biol, 1996, 264:1028-43.

Kozlowski A, et al., "Development of pegylated interferons for the treatment of chronic hepatitis C." 2001 BioDrugs, 15:419-429.

Krasnykh V, et al., "Characterization of an Adenovirus Vector Containing a Heterologous Peptide Epitope in the HI Loop of the Fiber Knob," J Virology, (1998) 72, pp. 1844-1852.

Lan et al., "Isolation and properties of a human pancreatic adenocarcinoma-associated . . . ," 1985 Cancer Res 45:305-310.

Lanni et al., "p53-independent apoptosis induced by paclitaxel through an indirect mechanism," 1997 Proc Natl Acad Sci 94:9679-9683.

Lavis et al., "Tuning the pKa of Flourescein to Optimize Binding Assays," 2007 Anal Chem, 79:6775-6782.

Laznicek, et al. "Pharmacokinetics and Distribution of Ribonuclease and its Monomethoxypoly(Ethylene Glycol) Derivatives in Rats" Pharmacological Research, vol. 28, No. 2, Sep. 1, 1993, pp. 153-162.

Leland, P.A. et al., "Cancer Chemotherapy—Ribonucleases to the Rescue," Chem and Biology. Apr. 2001, 8:405-413.

Leland, P.A., et al., "Endowing Human Pancreatic Ribonuclease with Toxicity for Cancer Cells," Journal of Biological Chemistry, (2001) 276(46), pp. 43095-43102.

Pous J., et al, "Three-dimensional Structure of a Human Pancreatic Ribonuclease Variant, a Step Forward in the Design of Cytotoxic Ribonucleases," J Mol. Biol., (2000) 303, pp. 49-60.

Leland, P.A., et al., "Ribonuclease a Variants with Potent Cytotoxic Activity," Proc. Natl. Acad. Sci., 95, pp. 10407-12 (1998).

Leonidas D.D., et al, "Binding of phosphase and pyrophosphate isons at the active site of human angiogenin as revealed by X-ray crystallography," Protein Sci., (2001) 10, pp. 1669-1676.

Leung D., et al., "A Method for Random Mutagenesis of a defined DNA Segment using . . . ," Technique, (1989) 1(1), pp. 11-15.

Lin, M.C., "The Structural Roles of Amino Acid Residues Near the Carboxyl Terminus of Bovine Pancreatic Ribonuclease A," J. Biol. Chem., 245, pp. 6726-6731 (1970).

Mallorqui-Fernandez, G., et al., "Three-dimensional Crystal Structure of Human Eosinophil Cationic Protein (RNase 3) at 1.75 A Resolution," J. Mol. Biol., (2000) 300, pp. 1297-1307.

Matousek et al. "PEG chains increase aspermatogenic and antitumor activity of RNase A and BS-RNase enzymes" Journal of Controlled Release 82 (2002) 29-37.

Matousek J, "Ribonucleases and their antitumor activity," 2001, Comp Biochem Physiology Tox Pharma, 129, pp. 175-191.

Matousek, et al. "Effect of hyaluronidase and PEG chain conjugation on the biologic and antitumor activity of RNase A" Journal of Controlled Release, vol. 94, No. 2-3, Feb. 10, 2004, pp. 401-410.

McGrath M., et al., "Immunotoxin Resistance in Multidrug Resistant Cells," Cancer Research, (2003) 63, pp. 72-79.

McKie, R., "Cancer Research Set Back a Decade," The Observer. 2001, (Jun. 10), pp. 1-4.

McLane K, "Transplantation of a 17-amino acid a-helical DNA-binding domain into an antibody molecule confers sequence-dependent DNA recognition," Proc. Natl. Acad. Sci., (1995) 92, pp. 5214-5218.

Merlino, A., et al., "The importance of Dynamic Effects on the Enzyme Activity X-ray Structure and Molecular Dynamics of Onconase Mutants," J Biol Chem 2005, 280:17953-17960.

(56) References Cited

OTHER PUBLICATIONS

Michaelis, et al. "Coupling of the antitumoral enzyme bovine seminal ribonuclease to polyethylene glycol chains increases its systemic efficacy in mice" Anti-Cancer Drugs, vol. 13, No. 2, Feb. 2002, pp. 149-154.
Miller, K.D. and Sledge, G.W. Jr, "Taxanes in the treatment of breast cancer: a prodigy comes of age," 1999 Cancer Investigation, 17:121-136.
Milton Harris J et al: "Effect of Pegylation on Pharmaceuticals" Nature Reviews. Drug Discovery, vol. 2, No. 3, Mar. 1, 2003, pp. 214-221.
Mitchell et al., "Interfaces in Molecular Docking," Molec. Simul. (2004) 30, pp. 97-106.
Mohan C.G., et al, "The Crystal Structure of Eosinophil Cationic Protein in Complex with 2′,5′-ADP at 2.0 A Resolution Reveals the Details of the Ribonucleolytic Active Site," Biochemistry, (2002) 41, pp. 12100-12106.
Moore J., et al., "Directed evolution of a para-nitrobenzyl esterase for aqueous-organic solvents," Nature Biotechnology, (1996) 14, pp. 458-467.
Mosimann S.C., et al, "X-ray Crystallographic Structure of Recombinant Eosinophil-derived Neurotoxin at 1.83 A Resolution," J. Mol. Biol., (1996) 260, pp. 540-552.
Narang S., "DNA Synthesis," Tetrahedron Report, (1983) 39(1), pp. 3-22.
Newton, D.L., et al., "Cytotoxic Ribonuclease Chimeras Tergeted Tumoricidal Activity in-vitro and in-vivo," Journal of Biological Chemistry, (1992) 267(27), pp. 19572-19578.
Newton, D.L., et al., "Potent and specific antitumor effects of an anti-CD22-targeted cytotoxic ribonuclease . . ." Blood, (2001) 97(2), pp. 528-535.
Nguyen, D.M., et al., "Impact of Transfusion of Mediastinal Shed Blood on Serum Levels of Cardiac Enzymes," Ann. Thorac. Surg. 1996, 62, pp. 109-114.
Ottl et al., "Preparation and Photoactivation of Caged Fluorophores and Caged Proteins Using a New Class of Heterobifunctional, Photocleavable Cross-Linking Reagents," 1998 Bioconj Chem 9:143-151.
Papageorgiou A.C., et al., "Molecular recognition of human angiogenin by placental ribonuclease inhibitor—an X-ray crystallographic study at 2.0 Å resolution," EMBO J., (1997) 16, pp. 5162-5177.
Pouckova, et al. "Polymer-conjugated bovine pancreatic and seminal ribonucleases inhibit growth of human tumors in nude mice" Journal of Controlled Release, vol. 95, No. 1, Feb. 20, 2004, pp. 83-92.
Park et al., "Anti-HER2 immunoliposomes for targeted therapy of human tumors," 1997 Cancer Lett 118:153-160.
Pegram et al., "Phase II Study of Intravenous Recombinant Humanized Anti-p185 HER-2 Monoclonal Antibody (rhuMAb HER-2) Plus Cisplatin in Patients with HER-2/NEU Overexpressing Metastatic Breast Cancer", 1995 Am Soc Clin Oncol 14:106.
Piccoli, Renate et al., "A dimeric mutant of human pancreatic ribonuclease with selective cytotoxicity toward malignant cells," 1999, Pro Nat Acad Sci, 96, pp. 7768-7773.
Potenza, N, et al., "Hybridase activity of human ribonuclease-1 revealed by a real-time fluorometric assay," Nucleic Acids Res, 2006, 34(10), pp. 2906-2913.
Monfardini et al., "A Branched Monomethoxypoly(ethylene glycol) for Protein Modification" Bioconjugate Chem. 1995, 6(1): 62-69.
Rutkoski et al., "Disruption of Shape-Complementarity Markers to Create Cytotoxic Variants of Ribonucleases A". J Molecular Biology 2005, 354(1): 41-54.

Asai, T. et al. "An interaction between S tag and S protein derived from human ribonuclease 1 allows site-specific conjugation of an enzyme to an antibody for targeted drug delivery," 2005 J Immun Meth, 299:63-76.

Backer M et al., "Adapter Protein for Site-Specific conjugation of Payloads for Targeted Drug Delivery," 2004 Bioconjugate Chem 15:1021-9.

Backer, M.V. et al., 2003, "Humanized docking system for assembly of targeting drug delivery complexes," J Cont Release, 89:499-511.

Bal, H., et al, "Human pancreatic ribonuclease Deletion of the carboxyl-terminal EDST extension enhances ribonuclease activity and thermostability," Eur. J. Biochem., 245, pp. 465-469 (1997).

Ban et al., "Interface Surfaces for Protein-Protein Complexes", Proc. 8th Ann. Intl. Conf. Res. Comp. Mol.Biol., (2004) pp. 205-212.

Benito, A., et al., "Stabilization of human pancreatic ribonuclease through mutation at its N-terminal edge," Protein Eng., 15, pp. 887-893 (2002).

Binkley et al., "RNA ligands to human nerve growth factor ," 1995 Nuc Acids Res 23(16):3198-205.

Boix E., et al., "Crystal Structure of Eosinophil Cationic Protein at 2.4 A Resolution," Biochemistry, (1999) 38, pp. 16794-16801.

Bosch, M., et al., "A Nuclear Localization Sequence Endows Human Pancreatic Ribonuclease with Cytotoxic Activity," Biochemistry, 43, pp. 2167-2177 (2004).

Bretscher, Leland, et al., "A Ribonuclease a variant with low catalytic activity but potent cytotoxic activity," J Biol. Chem., (2000) 275, 9893-9896.

Cadwell R.C., et al., "Randomization of Genes by PCR Mutagenesis," PCR Methods and Applications, (1992) 1(4), pp. 28-33.

Capala et al., "Boronated Epidermal Growth Factor as a Potential Targeting Agent for Boron Neutron Capture Therapy of Brain Tumors," 1996 Bioconjugate Chem 7:7-15.

Crameri A., et al., "Improved Green Flourescent Protein by Molecular Evolution," Nature Biotechnology, (1996)14, pp. 315-319.

Crameri A., et al., "Molecular evolution of an arsenate detoxification pathway by DNA shuffling," Nature Biotechnology, (1997) 15, pp. 436-438.

Curran, T.P., et al., "Alteration of the Enzymatic Specificity of Human Angiogenin by Site-Directed Mutagenesis," Biochemistry 32, pp. 2307-2313 (1993).

Cwirla S., et al., "Peptides onphage: A vast library of peptides for identifying ligands," Proc. Natl. Acad. Sci., (1990) 87, pp. 6378-6382.

Davis et al., Basic Methods in Molecular Biology. (1986).

De Lorenzo, C., "A Fully Human Antitumor ImmunoRNase Selective for ErbB-2-Positive Carcinomas," Cancer Res., (2004) 64, pp. 4870-4874.

Del Cardayre & Raines, "Structural Determinants of Enzymatic Processivity", 1994 Biochem 33:6031-6037.

Deonarain, M.P. et al., "Targeting enzymes for cancer therapy: Old Enzymes in New Roles." British Journal of Cancer, Nov. 1994 70(5):786-794.

Dermer, GB, "Another Anniversary for the War on Cancer," Bio/Technology. Mar. 12, 1994, p. 320.

Devlin J., et al., "Random Peptide Libraries: A source of specific protein Binding molecules," Science, (1990) 249, 404-406.

Dharap, S.S. et al., "Molecular Targeting of Drug Delivery Systems to Ovarian Cancer . . . " Journal of Controlled Release, (2003) 91, pp. 61-73.

Di Gaetano, G., et al., "Second generation antitumour human RNase: significance of its structural and functional features for the mechanism of antitumour action," Biochem. J., 358, pp. 241-247 (2001).

Dickson, K A, et al., "Compensating effects on the cytotoxicity of ribonuclease A variants," 2003 Archives Biochem and Biophysics, Acad Press, 415:172-177.

Domachowske et al., "Evolution of antiviral activity in the ribonuclease A gene superfamily . . . ," Nucleic Acids Res 26 (23): 5327-32 (1998).

Eckert K., et al., "DNA Polymerase Fidelity and the Polymerase Chain Reaction," PCR Methods and Applications, (1991) 1(1), pp. 17-24.

Fisher, B.M., et al., "Coulombic Forces in Protein-RNA Interactions: Binding and Cleavage by Ribonuclease A and Variants at Lys7, Arg10, and Lys66," Biochemistry, 37, pp. 12121-12132 (1998).

Francis et al., Stability of protein pharmaceuticals: in vivo pathways of degradation and strategies for protein stabilization (Eds. Ahern., T. and Manning, M.C.) Plenum, N.Y., pp. 247-251 (1991).

(56) References Cited

OTHER PUBLICATIONS

Futami J., et al., "Inhibition of cell growth by a fused protein of human ribonuclease 1 and human basic fibroblast growth factor" Protein Engineering, (1999) 12(11) pp. 1013-1018.

Gaur, D. et al., "Interaction of human pancreatic ribonuclease with human ribonuclease inhibitor. Generation of inhibitor-resistant cytotoxic variants," J. Biol. Chem., 276:24978-24984 (2001).

Gluzman Y., "SV40-transformed Simian Cells Support the Replication of Early SV40 Mutants," Cell, (1981) 23, pp. 175-182.

Goldberg and Baldwin, "A specific transition state for S-peptide combining with folded S-protein and then refolding," 1999 PNAS 96:2019-2024.

Gorman, C., et al. "The Hype and the Hope" Time. 1998, 151(19) pp. 40-44.

Gura, T., "Systems for Identifying New Drugs are Often Faulty," Science. 1997, 278(Nov. 7), pp. 1041-1042.

Gutte B., et al., "The synthesis of ribonuclease A," Journal of Biological Chemistry, (1971) 246(6), pp. 1922-1941.

Haldar et al., "Bcl2 Is the Guardian of Microtubule Integrity," 1997 Cancer Research 57:229-233.

Hamachi et al., "Design and semisynthesis of spermine-sensitive ribonucleases S" 1999 Bioorg Med Chem Lett 9:1215-1218.

Hanisch et al., "Structural studies on oncofetal carbohydrate antigens (Ca 19-9, Ca 50, and Ca 125) carried by O-linked sialyloligosaccharides on human amniotic mucins," 1988 Carbohydr Res 178:29-47.

Harder J., et al, "RNase 7, a Novel Innate Immune Defense Antimicrobial Protein of Healthy Human skin," J. Biol. Chem., (2002) 277, pp. 46779-46784.

Hinoda et al., "Immunochemical characterization of adenocarcinoma-associated antigen yh206," 1988 Cancer J 42:653-658.

Hursey, M., et al., "Specifically Targeting the CD22 Receptor of Human B-Cell Lymphomas With RNA . . . " Leukemia & Lymphoma, (2002) 43(5), pp. 953-959.

Ike Y., et al., "Solid phase synthesis of polynucleotides," Nucleic Acids Research, (1983) 11(2), pp. 477-488.

Ishida et al., "Related Glycoproteins from Normal Secretory and Malignant Breast Cells," 1989 Tumor Biol 10:12-22.

Itakura K., et al., "Chemical Synthesis . . . " Recombinant DNA, in Walton (ed.),Proceedings of 3rd Cleveland Symposium, (1981) pp. 273-289.

Itakura K., et al., "Synthesis and Use of Synthetic Oligonucleotides," Ann. Rev. Biochem., (1984) 53, pp. 323-356.

Iyer S., et al, "Molecular Recognition of Human Eosinophil-derived Neurotoxin (RNase 2) by Placental Ribonuclease Inhibitor," J Mol. Biol., (2005) 347, pp. 637-655.

Jellinek et al., "Inhibition of receptor binding by high-affinity RNA ligands to vascular endothelial growth factor," 1994 Biochem 33(34):10450-6.

Jinno H., et al., "The Cytotoxicity of a Conjugate Composed of Human Epidermal Growth Factor," Anticancer Res., (2002) 22, pp. 4141-4146.

THERAPEUTIC RIBONUCLEASES

CROSS-REFERENCE TO RELATED APPLICATIONS

The present application is a continuation of U.S. Pat. No. 8,628,768, filed Jul. 10, 2012, which is a continuation of U.S. Pat. No. 8,216,567, filed Sep. 13, 2011, which is continuation of U.S. Pat. No. 8,029,782, filed Oct. 1, 2009, which claims priority to U.S. Provisional Patent Application Ser. No. 61/101,905, filed Oct. 1, 2008, each of which is herein incorporated by reference in its entirety.

FIELD OF THE INVENTION

The present invention relates to the use of ribonucleases (RNases) in the treatment or prevention of disease.

BACKGROUND OF THE INVENTION

In the U.S. population, mortality associated with the 15 most common cancer types alone has been estimated to approach 170 deaths annually per 100,000 individuals (Martin L Brown, Joseph Lipscomb and Claire Snyder, 2001, THE BURDEN OF ILLNESS OF CANCER: Economic Cost and Quality of Life, Ann. Rev. Public Health, 22: 91-113). Currently, there are an estimated 1,437,180 new cases of cancer and 565,650 deaths each year (American Cancer Society *Cancer Facts and Figures* 2008). The economic burden of cancer has been estimated to exceed $96B in 1990 dollars (Brown et al, 2001).

The term "chemotherapy" simply means the treatment of disease with chemical substances. The father of chemotherapy, Paul Ehrlich, imagined the perfect chemotherapeutic as a "magic bullet;" such a compound would kill invading organisms or cells without harming the host. While significant progress has been made in identifying compounds that kill or inhibit cancer cells and in identifying methods of directing such compounds to the intended target cells, the art remains in need of improved therapeutic compounds.

There are a range of different types of chemotherapeutic agents available, including small molecules and biologics such as nucleic acid compounds, polypeptide compounds, or derivatives thereof. In general, properties of chemotherapeutics requiring consideration include efficacy, pharmacokinetic properties, and ease of manufacture. Protein therapeutics in general may offer particular advantages as alternatives to small molecules; however, effective protein drugs must have a balance of optimal properties that include specificity, cytotoxicity, affinity for their target, safety, solubility, amenability to effective delivery, stability, and longevity in the body (clearing time). A candidate drug having superiority in any one of these properties may not possess the optimal balance of features overall to serve as an effective drug.

There is need in the art for additional anti-cancer chemotherapeutics that have an effective complement of features for use in therapeutic settings.

SUMMARY OF THE INVENTION

The present invention relates to the use of RNases in the treatment or prevention of disease. In some embodiments, RNases are used for the treatment or prevention of human disease such as cancer. In some embodiments, a variant of recombinant human RNase 1 has an optimal balance of desirable properties for the treatment or prevention of human cancer. Such properties include but are not limited to stability, cytotoxicity towards pathogenic cells, efficacy of degradation of pathogenic RNA of any origin including viral RNA, evasion of binding by RNase inhibitors, resistance to degradation by proteases, delivery to target cells, efficiency of import into the cell, dose response properties, pharmacokinetic properties, and longevity within the human body. In some embodiments, therapeutic compositions and methods of the invention employ a variant of human RNase 1 that has amino acid changes compared to a wild type enzyme: R4C, G38R, R39G, N67R, G89R, S90R, and V118C. In some embodiments, the ribonuclease comprises or consists of SEQ ID NO:1:

```
KESCAKKFQRQHMDSDSSPSSSSTYCNQMMRRRNMTQRGCKPVNTFVHEP
LVDVQNVCFQEKVTCKRGQGNCYKSNSSMHITDCRLTNRRRYPNCAYRTS
PKERHIIVACEGSPYVPCHFDASVEDST.
```

In some embodiments, the amino acid sequence comprises or consists of SEQ ID NO:1 having an N-terminal methionine (SEQ ID NO:4):

```
MKESCAKKFQRQHMDSDSSPSSSSTYCNQMMRRRNMTQRGCKPVNTFVHE
PLVDVQNVCFQEKVTCKRGQGNCYKSNSSMHITDCRLTNRRRYPNCAYRT
SPKERHIIVACEGSPYVPCHFDASVEDST.
```

In some embodiments, the ribonuclease is recombinantly produced. In some embodiments, the ribonuclease is encoded by a nucleic acid molecule comprising SEQ ID NO:2:

```
AAA GAA TCT TGC GCT AAA AAA TTC CAG CGT CAG CAC ATG GAC TCT GAC
TCT TCT CCG TCT TCT TCT TCT ACT TAC TGC AAC CAG ATG ATG CGT CGC
CGT AAC ATG ACT CAG CGT GGT TGC AAA CCG GTT AAC ACT TTC GTT CAT
GAA CCG CTG GTT GAC GTT CAG AAC GTT TGC TTC CAG GAA AAA GTT ACT
TGC AAA CGC GGT CAG GGT AAC TGC TAC AAA TCT AAC TCT TCT ATG CAT
ATC ACT GAC TGC CGT CTG ACG AAT CGT CGC CGT TAC CCG AAC TGC GCT
TAC CGT ACT TCT CCG AAA GAA CGT CAT ATC ATC GTT GCT TGC GAA GGT
TCT CCG TAC GTT CCG TGT CAT TTC GAC GCT TCT GTT GAA GAC TCT ACC
```

In some embodiments, an expression vector encoding the ribonuclease further comprises a leader sequences, such as SEQ ID NO:3:

```
TT GNT TAA CTT TAA GAA GGA GAT ATA CATATG
```

In some embodiments, an expression vector encoding the ribonuclease further comprises one or more stop codons (e.g., TAA and/or TGA).

In some embodiments, the RNase is conjugated to water-soluble moieties as a means of providing improved physical properties. In some embodiments, the water-soluble moiety is a polyethylene glycol (PEG) molecule. In some embodiments, the RNase is conjugated or fused to, or otherwise associated with, a moiety that targets the RNase to a specific cell type, such as a diseased or cancerous cell.

Thus, in some embodiments, the present invention provides a composition (e.g., a therapeutic preparation) comprising a ribonuclease (e.g., a purified ribonuclease) having a human RNase 1 sequence with amino acid modifications: R4C, G38R, R39G, N67R, G89R, S90R, and V118C (e.g., comprising or consisting of SEQ ID NO:1). In some embodiments, the present invention provides an expression vector comprising a nucleic acid sequence encoding such a ribonuclease (e.g., comprising SEQ ID NO:2). In some embodiments, the present invention provides a host cell comprising such an expression vector. In some embodiments, the present invention further provides methods of treating subjects (e.g., human subject suffering from or suspected of suffering from cancer) by administering a ribonuclease, alone or in combination with other agents, to the subject. The administration may be at one or more time points in a therapeutically effective dose (e.g., administered at 0.01 to 100 mg/kg body weight of the subject per week for one or more weeks; per day for one or more days; or per treatment for one or more treatments).

As used herein, the term "variant of a ribonuclease" refers to a modified ribonuclease that retains enzymatic activities similar to that (e.g., that has at least 60%, at least 75%, at least 85%, at least 95%, or at least 99% of activity retained) associated with the non-modified ribonuclease from which it was derived. Tests for measuring enzymatic activities are described herein and are known in the art. The variant may be a variant of a natural enzyme or may be a variant of a non-natural enzyme. For example, a particular non-natural synthetic ribonuclease having SEQ ID NO:1 may be modified to include one or more amino acid changes that result in a variant of SEQ ID NO:1. In some preferred embodiments, the variant has one or a limited number of amino acid substitutions (e.g., conservative or non-conservative substitutions), additions, or deletions (e.g., truncations) compared to the non-modified ribonuclease.

As used herein, the term "variant of a ribonuclease retaining RNA degradation activity" refers to a variant of ribonuclease (e.g., SEQ ID NO:1) that has at least 50%, at least 60%, at least 75%, at least 85%, at least 95%, or at least 99% of RNA degradation activity of the non-modified ribonuclease from which it was derived. RNA degradation activity may be measured using any suitable assay including, but not limited to, visualization and quantitation of a degraded RNA sample using agarose or polyacrylamide gel electrophoresis. In some preferred embodiments, the variant has one or a limited number of amino acid substitutions (e.g., conservative or non-conservative substitutions), additions, or deletions (e.g., truncations) compared to the non-modified ribonuclease.

As used herein, the term "variant of a ribonuclease having substantially the same cell killing activity, cytotoxic activity, cytostatic activity, or cell damaging activity" refers to a variant of a ribonuclease (e.g., SEQ ID NO:1) that has at least 50%, at least 60%, at least 75%, at least 85%, at least 95%, or at least 99% of the cell killing activity, cytotoxic activity, cytostatic activity, or cell damaging activity of the non-modified ribonuclease from which it was derived. For example, in some embodiments, the activity is the ability to kill or otherwise affect cancer cells. In other embodiments, it is the ability to reduce tumor size in animals. In yet other embodiments, the activity is the ability to reduce symptoms of a disease characterized by aberrant cell growth (e.g., cancer). Activity may be measured using any suitable method including, but not limited to, commercially available cell viability assays, measurement of tumor size, and commercially available cell proliferation assays. In some preferred embodiments, the variant has one or a limited number of amino acid substitutions (e.g., conservative or non-conservative substitutions), additions, or deletions (e.g., truncations) compared to wild type enzyme.

As used herein, the term "variant of a ribonuclease retaining protein folding properties" refers to a variant of a ribonuclease (e.g., SEQ ID NO:1) that exhibits similar protein folding properties as the non-modified ribonuclease from which it was derived. Protein folding properties include speed of protein folding and folding of proper structure (folding that substantially retains the activity of the non-modified ribonuclease from which it was derived). In preferred embodiments variants fold with at least 50%, at least 60%, at least 75%, at least 85%, at least 95%, or at least 99% or more of the speed of the non-modified ribonuclease from which it was derived. Assays for protein folding are well known in the art and include, but are not limited to, spectroscopic and enzymatic (e.g. RNA degradation) assays and HPLC. In some preferred embodiments, the variant has one or a limited number of amino acid substitutions (e.g., conservative or non-conservative substitutions), additions, or deletions (e.g., truncations) compared to wild type enzyme.

As used herein, the term "variant of a ribonuclease having similar immunogenicity properties" refers to a variant of a ribonuclease (e.g., SEQ ID NO:1) that, in some embodiments, exhibits substantially the same or better immunogenicity properties than the non-modified ribonuclease from which it was derived. Immunogenicity properties include toxicity and undesirable immune responses (e.g., cytotoxic immune response) in animals. In preferred embodiments, variants exhibit less than 100%, preferably less than 90%, even more preferably less than 80%, and still more preferably less than 70% of the toxicity or undesirable immune response of the non-modified ribonuclease from which it was derived. The level of toxicity or immunogenicity can be determined using any suitable method including, but not limited to, commercially available assays for toxicity and immune response (e.g., measurement of cytokines or T-cell response). In some preferred embodiments, the variant has one or a limited number of amino acid substitutions (e.g., conservative or non-conservative substitutions), additions, or deletions (e.g., truncations) compared to wild type enzyme.

The term "heterologous nucleic acid sequence" or "heterologous gene" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance or therapeutic benefits), etc.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IgE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes subjects who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

As used herein, the term "subject at risk for cancer" refers to a subject with one or more risk factors for developing a specific cancer. Risk factors include, but are not limited to, gender, age, genetic predisposition, environmental exposure, and previous incidents of cancer, preexisting non-cancer diseases, and lifestyle.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

"Amino acid sequence" and terms such as "polypeptide" or "protein" are not meant to limit the amino acid sequence to the complete, native amino acid sequence associated with the recited protein molecule.

The terms "test compound" and "candidate compound" refer to any chemical or biological entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present invention.

The term "gene" refers to a nucleic acid (e.g., DNA) sequence that comprises coding sequences necessary for the production of a polypeptide or precursor (e.g., ribonucleases or ribonuclease conjugates of the present invention). The polypeptide can be encoded by a full length coding sequence or by any portion of the coding sequence so long as the desired activity or functional properties (e.g., enzymatic activity, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions with its various ligands and/or substrates. In some embodiments, fragments posses an activity of the native protein.

As used herein, the term "purified" or "to purify" refers to the removal of impurities and contaminants from a sample. For example, antibodies are purified by removal of non-immunoglobulin proteins; they are also purified by the removal of immunoglobulin that does not bind an intended target molecule. The removal of non-immunoglobulin proteins and/or the removal of immunoglobulins that do not bind an intended target molecule results in an increase in the percent of target-reactive immunoglobulins in the sample. In another example, recombinant polypeptides are expressed in host cells and the polypeptides are purified by the removal of host cell proteins; the percent of recombinant polypeptides is thereby increased in the sample.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

DETAILED DESCRIPTION OF THE INVENTION

The present invention provides ribonuclease compositions and methods. The ribonucleases find use as pharmaceutical agents and as research agents (e.g., for studying or characterizing biological processes in cells, tissues, or organisms). For example, in some embodiments, ribonucleases comprising SEQ ID NO:1 are provided. SEQ ID NO:1 is the native human RNase 1 with amino acid modifications: R4C, G38R, R39G, N67R, G89R, S90R, and V118C (X#Y, where X is the native amino acid, # is the amino acid position based on a recognized numbering system for human RNase 1, and Y is the modified amino acid that replaces X). The present invention also provides variants of SEQ ID NO:1 that maintain the 4C, 38R, 39G, 67R, 90R, and 118C sequences, but include one or more additional amino acid changes. A variety of variants are described in more detail below.

The ribonucleases of the invention were identified based on a balance of a number of properties to yield an effective therapeutic molecule. Properties considered included stability, cytotoxicity towards pathogenic cells, efficacy of degradation of pathogenic RNA of any origin including viral RNA, evasion of binding by RNase inhibitors, resistance to degradation by proteases, delivery to target cells, efficiency of import into the cell, dose response properties, pharmacokinetic properties, and longevity within the human body. For example, the ribonuclease of SEQ ID NO:1 provides a useful therapeutic molecule that has a balance of properties making it superior to prior described therapeutic ribonucleases, such as QBI-119 described in U.S. Pat. Publ. Ser. No. 20050261232 (herein incorporated by reference in its entirety). The ribonuclease of SEQ ID NO:1 is inferior to QBI-119 and native human RNase 1 in certain characteristics that might be considered important in selecting an optimal compound (e.g., enzyme activity, ribonuclease inhibitor evasion, etc.), yet provides an overall superior therapeutic agent. For example, SEQ ID NO:1 has only a fraction of the of the ribonuclease activity of native human RNase1 (less than 1%), yet is therapeutically effective.

The ribonucleases of the present invention find use in treating a wide variety of disease states, including a wide variety of cancer types. For example, SEQ ID NO:1 was tested against non-small cell lung cancer cells (A549 cell line), pancreatic cancer cells (BxPC3 cell line), and prostate cancer cells (DU145 cell line) and found to inhibit tumor growth greater than 65% (and as high as 94%) with dose ranges of 15 mg/kg-100 mg/kg given 1 to 5 times per day or week. This was superior to QBI-119 both with respect to the percent of inhibition (which was equal to or better than QBI-119) and the diversity of cancer cell types at which it was highly efficacious.

The ribonucleases of the present invention may be formulated in any desired form with or without other therapeutic agents, carriers, excipients, or other components (e.g., targeting moieties, water-soluble molecules, and the like). The ribonucleases may be packaged into kits, containing packaging and appropriate containers for shipment and/or storage as therapeutic or research agents, including preparation into dosage form for single or multiple doses for one or more patients.

The present invention further provides variants of SEQ ID NO:1, including amino acid variations that do not significantly alter one or more or any therapeutically relevant properties of the ribonuclease. Examples of these variants are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of ribonucleases disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (including, but not limited to, FADE (Mitchell et al., (2004). Molec. Simul. 30, 97-106); MAPS (Ban et al., Proceedings of the 8th Annual International Conference on Research in Computational Molecular Biology, 2004, 205-212), SYBYL (Tripos, Inc, St. Louis, Mo.); and PyMOL (available on the Internet web site of sourceforge)).

Crystal structures of RNase 1 are described, for example in Pous et al. (Acta Crystallogr D Biol Crystallogr. 2001; 57, 498-505) and Pous et al. (J Mol. Biol. 2000; 303, 49-60) and serve as the basis for selection of changes. In addition, crystal structures are available for other human pancreatic ribonucleases, including eosinophil derived neurotoxin (EDN, RNase 2; Swaminathan et al, Biochemistry, 2002, 41, 3341-3352, Mosimann et al J. Mol. Biol., 1996, 260, 540-552; Iyer et al J Mol Biol, 2005, 347, 637-655), eosinophil cationic protein (ECP, RNase 3; Mohan et al Biochemistry 2002; 41, 12100-12106; Boix et al Biochemistry, 1999, 38, 16794-16801; Mallorqui-Fernandez et al J. Mol. Biol, 2000, 300, 1297-1307), RNase 4 (Terzyan et al, 1999, 285, 205-214) and angiogenin (RNase 5; Leonidas et al J. Mol. Biol. 1999, 285, 1209-1233; Leonidas et al Protein Sci., 2001, 10, 1669-1676; Papageorgiou et al EMBO J., 1997, 16, 5162-5177; Shapiro et al J. Mol. Biol., 2000, 302, 497-519).

Variants may be produced by methods such as directed evolution or other techniques for producing combinatorial libraries of variants, described in more detail below. In still other embodiments of the present invention, the nucleotide sequences of the present invention may be engineered in order to alter a human RNase coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.). In some embodiments, changes are made in the nucleic acid sequence encoding a polypeptide of the present invention in order to optimize codon usage to the organism that the gene is expressed in.

Exemplary variants are described below, including, but not limited to, substitutions, truncations, chimeras, etc. The present invention is not limited to these particular variants. Both variants in the active site and substrate-binding region and away from the active site are contemplated to be within the scope of the present invention. For example, variants of SEQ ID NO:1 include the R4C, G38R, R39G, N67R, G89R, S90R, and V118C changes compared to normal human RNAse 1, but also contain one or more additional changes that either impact or do not impact one or more of the activities or properties of the enzyme. Variants may be selected based on, for example, experimental data, computer modeling, and by rational design by comparison to other ribonucleases. Activities may be tested using assays to select the variants with the desired properties (see e.g., Raines et al., J. Biol. Chem., 273, 34134 (1998); Fisher et al., Biochemistry 37:12121 (1998); Guar et al., J. Biol. Chem., 276:24978 (2001); Bosch, et al., Biochemistry, 43:2167 (2004); Lin, J. Biol. Chem., 245:6726 (1970); Bal et al, Eur. J. Biochem., 245:465 (1997); Guar et al., Mol. Cell. Biochem., 275:95 (2005); Benito et al., Protein Eng., 15:887 (2002); Ribo et al., Biol. Chem. Hoppe-seyler, 375:357 (1994); DiGaetano et al., Biochem. J., 358:241 (2001); Trautwein et al., FEBS Lett., 281:277 (1991); Curran et al., Biochemistry 32:2307 (1993); Sorrentino et al., Biochemistry 42:10182 (2003); herein incorporated by reference in their entireties).

Exemplary amino acid locations for modification in the production of variants are provided below. One or more sites may be modified, as desired. The exemplary list below provides a ranking of the utility for modification of each amino acid position based on the amino acid numbering of a wild-type human RNase 1 (e.g., as represented by interest in modifying (e.g., so as to result in a functional ribonuclease (e.g., comprising a desired property (e.g., cancer cell killing and/or ribonucleolytic activity))). An "interest site" may be characterized as a "high interest site," a "medium interest site," or a "low interest site" based on characteristics of the ribonuclease described herein (e.g., biologic activity (e.g., ribonucleolytic activity, cancer cell killing activity, oligomerization capacity, etc.)) desired to be retained within the ribonuclease after modification of the same (e.g., for deletion, substitution or other type of mutation to create a ribonuclease variant, and/or for conjugation to a water-soluble polymer). For example, high interest sites are those that can be modified without significantly interfering with one or more desired activities or properties of the ribonuclease: High interest (1-3, 13-24, 31-39, 48-50, 60, 66-71, 75-78, 87-94, 105, 112-115, and 127-128); Medium interest (4-11, 25, 27-30, 42-47, 51-57, 59, 61-64, 73-74, 79-83, 85-86, 96-104, 106-109, 111, 116-118, and 120-126); and Low interest (12, 26, 40-41, 58, 65, 72, 84, 95, 110, and 119).

It will be appreciated that one or more modification sites may be used. Preferably, the selected sites are high or medium interest sites. However, one or more additional sites may be altered as desired and appropriate for the intended application. It should be noted that, in some embodiments, RNase is produced in such a way that a methionine (e.g., that is not part of wild type human RNase) is incorporated as the first amino acid of the protein (e.g., via the methods used to produce the protein (e.g., recombinant human ribonuclease (e.g., produced in $E.\ coli$))). Thus, in some embodiments, the numbering of amino acid residues depicted herein may be off by a numerical value of one (e.g., if a methionine is incorporated into the protein, then the numbering of the amino acid residues of the human RNases recited herein is off by 1 (i.e., because a methionine is incorporated in position 1, the numbering of the amino acids depicted will be short by one, e.g., the residue number 10 would actually be residue number 11 because of the methionine incorporated at position 1)). Similarly, the positions depicted may also be applied to corresponding numerical positions other related ribonucleases.

In some embodiments, the desired residues for modification (e.g., deletion, mutation, etc.) in the present invention are selected to avoid disruption of the tertiary structure and/or stability of the ribonuclease. In some embodiments, these residues are on the surface of the protein (e.g., residues generally exposed to solvent (e.g., water or buffer)). For example, in some embodiments, the types of residues that are modified include, but are not limited to, amino acids that appear disordered in crystal structures, residues that contact the ribonuclease inhibitor protein, and amino acids not involved in tertiary structures (e.g., alpha helices and beta sheets), amino acids in loop regions between structures (e.g. alpha helices and beta sheets) as well as amino acids towards the end of the protein (the N- and C-termini). In some embodiments, additional amino acid residues are added to either the N- or C-terminus (e.g., to generate a RNase analogue and/or for conjugation of a water-soluble polymer).

In some embodiments, the present invention provides polymer conjugation of ribonucleases to increase its circulating half-life in vivo while retaining ribonuleolytic activity or other desired function (e.g., cancer cell killing). In some embodiments, the ribonuclease is conjugated to a water-soluble polymer in a region of the protein involved in evasion from ribonuclease inhibitor (RI). In some preferred embodiments, the ribonuclease is conjugated to a water-soluble polymer in a region of the protein that is not involved in evasion from RI (e.g., a region that has no impact on binding of the ribonuclease to the RI). Examples of regions that are not involved in evasion from RI include, but are not limited to, regions comprising amino acid residues at positions 1, 49, 75 or 113. Thus, although an understanding of the mechanism is not necessary to practice the present invention and the present invention is not limited to any particular mechanism of action, in some embodiments, conjugation of a water soluble polymer to ribonuclease possessing biological activity (e.g., cancer cell killing) even though the conjugation does not assist the ribonuclease from evading the RI.

In some embodiments, the present invention utilizes incorporation of a unique functional group in RNases for conjugation of a water-soluble polymer. For example, in some embodiments, a cysteine molecule is engineered into a RNase (e.g., without loss of ribonucleolytic activity or other desired function (e.g., cancer cell killing capacity)) in order to provide a free thiol group for conjugation to a water-soluble polymer. Free thiol groups are not found elsewhere in the RNase thereby providing the ability to generate a homogenous conjugation. In other embodiments, recombinant DNA technology is utilized to provide modified or novel codons to incorporate non-natural amino acids with orthogonal functionality into the RNase of interest (e.g., without loss of ribonucleolytic activity).

In some embodiments, ribonucleases are modified to include one or more amino acid residues such as, for example, lysine, cysteine and/or arginine, in order to provide an attachment location for water-soluble polymer (e.g., to an atom within the side chain of the amino acid). Techniques for adding amino acid residues are well known to those of ordinary skill in the art (See, e.g., March, Advanced Organic Chemistry: Reactions Mechanisms and Structure, 4th Ed. (New York: Wiley-Interscience, 1992).

The present invention is not limited by the type of modification made to said ribonuclease described herein. In some embodiments, the present invention is modified through the attachment of one or more moieties selected from the group comprising dextran, carbohydrate, albumin, carrier protein, and antibody (e.g., a non-targeting antibody used to extend the half-life of the ribonuclease).

The present invention is not limited by the type of water-soluble polymer utilized for conjugation to a human ribonuclease described herein. Indeed, any biocompatible water-soluble polymer may be used. In some embodiments, the water-soluble polymer is nonpeptidic, nontoxic, non-naturally occurring and/or biocompatible. A water-soluble polymer is considered biocompatible if the beneficial effects associated with use of the polymer alone or with another substance (e.g., conjugated to the ribonuclease) in connection with living tissues (e.g., administration to a patient) outweighs any deleterious effects as evaluated by a clinician (e.g., a physician). With respect to non-immunogenicity, a polymer is considered nonimmunogenic if the intended use of the polymer in vivo does not produce an undesired immune response (e.g., the formation of antibodies) or, if an immune response is produced, that such a response is not deemed clinically significant or important as evaluated by a clinician.

Thus, in some preferred embodiments, the water-soluble polymer is biocompatible and nonimmunogenic.

Water-soluble polymers of the present invention are selected such that, when attached to a human ribonuclease, the polymer does not precipitate in an aqueous environment, such as a physiological environment. In some embodiments, the polymer is selected based upon the method of conjugation to the human ribonuclease protein. For example, for methods utilizing reductive alkylation, the polymer selected should have a single reactive aldehyde so that the degree of polymerization may be controlled. The polymer may be branched or unbranched. Preferably, for therapeutic use of the end-product preparation, the polymer will be pharmaceutically acceptable. One skilled in the art will be able to select the desired polymer based on such considerations as whether the polymer/protein conjugate will be used therapeutically, and if so, the desired dosage, circulation time, resistance to proteolysis, and other considerations. For example, these may be ascertained by assaying for ribonucleolytic activity of the conjugate in vitro using methods well known in the art.

The water-soluble polymer may be selected from the group including, but not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(.alpha.-hydroxy acid), poly(vinyl alcohol), polyphosphazene, polyoxazoline, poly(N-acryloylmorpholine), and combinations of any of the foregoing.

The polymer may be linear (e.g., alkoxy PEG or bifunctional PEG) or branched. Furthermore, the polymer may be multi-armed (e.g., forked PEG or PEG attached to a polyol core), dendritic, and/or comprise degradable linkages. It is contemplated that the internal structure of the polymer can be organized in any of a number of different patterns (e.g., patterns including, but not limited to, homopolymer, alternating copolymer, random copolymer, block copolymer, alternating tripolymer, random tripolymer, and block tripolymer).

Furthermore, the polymer may be "activated" with a suitable activating group appropriate for coupling to a desired residue within the ribonuclease. An "activated" polymer refers to a polymer that possesses reactive groups for reaction with a ribonuclease. Examples of activated polymers and methods for their conjugation to proteins that are contemplated to be useful (e.g., for conjugating a water-soluble polymer to a human ribonuclease) in the present invention are known in the art and are described in detail in Zalipsky, Bioconjugate Chem 6, 150-165 (1995); Kinstler et al., Advanced Drug Delivery Reviews 54, 477-485 (2002); and Roberts et al., Advanced Drug Delivery Reviews 54, 459-476 (2002); each of which is hereby incorporated by reference in its entirety for all purposes.

The polymer may be of any molecular weight. For example, for polyethylene glycol, a preferred molecular weight is between about 2 kDa and about 150 kDa (the term "about" indicating that in preparations of polyethylene glycol, some molecules will weigh more, some less, than the stated molecular weight). Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic composition of the present invention (e.g., comprising a RNase protein or analog)).

When polyethylene glycol (PEG) is utilized as the water soluble polymer, PEG may have one of its termini capped with an inert group. For example, the PEG molecule may be methoxy-PEG, also referred to as mPEG, which is a form of PEG wherein one terminus of the polymer is a methoxy (e.g., —OCH$_3$) group, while the other terminus is a functional group (e.g., hydroxyl) that can be chemically modified and used for conjugation to a reactive group on a target protein (e.g., human ribonuclease). In some embodiments, a PEG polymer described in U.S. Pat. App. Pub. No. 20040235734 is used, herein incorporated by reference in its entirety.

In some embodiments, the PEG polymer may comprise one or more weak or degradable linkages. For example, a PEG polymer may comprise an ester linkage (e.g., that may hydrolyze over time (e.g., when present within a patient)). In some embodiments, hydrolysis of the PEG polymer comprising a degradable linkage produces two or more fragments (e.g., of lower molecular weight than the parent molecule).

The present invention is not limited by the type of degradable linkage. Indeed, a PEG polymer may comprise one or more of a variety of degradable linkages including, but not limited to, carbonate linkages; imine linkages; phosphate ester linkages; hydrazone linkages; acetal linkages; orthoester linkages; amide linkages, urethane linkages; peptide linkages; and oligonucleotide linkages.

It is contemplated that the inclusion of one or more degradable linkages within the polymer itself provides an added mechanism to control the pharmacokinetic characteristics of the conjugates of the present invention. For example, in some embodiments, a RNase-PEG conjugate of the present invention may be administered to a patient wherein the conjugate, when administered, possesses little to no enzymatic activity, but when exposed to conditions such that the linkages degrade (e.g., hydrolyze), the ribonucleolytic activity of the enzyme is activated. Thus, in some embodiments, the degradable linkages within the PEG molecule can be used for increasing specificity and efficacy of the conjugate.

It is contemplated that the conjugates of the present invention may comprise a linkage between the polymer (e.g., PEG) and human ribonuclease protein. In some embodiments, the linkage is a stable linkage (e.g., amide linkage, carbamate linkage, amine linkage, thioether/sulfide linkage, or carbamide linkage. In some embodiments, the linkage is hydrolytically degradable (e.g., to allow release of the RNase (e.g., without a portion of the polymer (e.g., PEG) remaining on the RNase)). The present invention is not limited by the type of degradable linkage utilized. Indeed, a variety of linkages are contemplated herein including, but not limited to, carboxylate ester, phosphate ester, thiolester, anhydrides, acetals, ketals, acyloxyalkyl ether, imines, orthoesters, peptides and oligonucleotides. These linkages may be prepared by modification of either the RNase protein (e.g., at the C-terminal carboxyl group, or a hydroxyl group of an amino acid side chain) and/or the polymer (e.g., using methods known in the art).

The proportion of water-soluble polymer (e.g., PEG) to ribonuclease protein molecules may vary, as may their concentrations in the reaction mixture. In general, the optimum ratio (e.g., in terms of efficiency of reaction (e.g., to conjugate polymer to one, two three, four or more sites) where there is little to no excess unreacted protein or polymer) can be determined (e.g., using the molecular weight of the polymer (e.g., PEG) selected, conjugation chemistry utilized, number of interest sites targeted, etc.). For example, in some embodiments, a non-specific conjugation reaction (e.g., PEGylation reaction) can be carried out followed by a later purification (e.g., to separate RNases based upon the number of polymers (e.g., PEGs) conjugated to each RNase).

In some embodiments, the conjugates are present within a composition. For example, in some embodiments, the composition comprises a plurality of conjugates, wherein each protein comprises 1-3 water-soluble polymers covalently attached to the protein. In some embodiments, the composition comprises a plurality of conjugates, wherein each protein comprise 1, 2, 3, 4, 5, 6, or more polymers attached to the protein. In some embodiments, the composition comprises a population of conjugates wherein the majority of conjugates (e.g., greater than 65%, greater than 70%, greater than 75%, greater than 80%, greater than 85%, greater than 90%, greater than 95%, greater than 97%, greater than 98%, greater than 99%) are covalently attached to the same number (e.g., 1, 2, 3, or more) of polymers (e.g., PEG molecules). In some embodiments, 1, 2, 3, or more polymers are conjugated to an oligomerized ribonuclease. The present invention is not limited by the number of ribonuclease molecules present within an oligomer. Indeed, a variety of oligomers may be conjugated to one or more water-soluble polymers including, but not limited to, oligomers of two, three, four, five, six, or even more ribonucleases. In some embodiments, the present invention provides a composition comprising a plurality of RNases that comprise a single water-soluble polymer (e.g., that are monoPEGylated). In some embodiments, the plurality of RNases comprise monomers, dimers, trimers, and/or higher order complexes (i.e., oligomers) of RNases.

In preferred embodiments, the modified human ribonuclease proteins (e.g., water-soluble polymer-RNase conjugates) of the present invention retain a significant portion of enzymatic (e.g., ribonucleolytic) activity. In some embodiments, the conjugate possesses from about 1% to about 95% of the enzymatic activity of the unmodified (e.g., non-conjugated) ribonuclease. In some embodiments, the conjugate possesses more activity than the unmodified ribonuclease. In some embodiments, a modified human ribonuclease possesses about 1%, 5%, 10%, 15%, 20%, 30%, 40%, 50%, 55%, 60%, 65%, 70%, 75%, 80%, 85%, 90%, 95%, 97%, 99%, 100%, or more relative to that of the unmodified parent ribonuclease possessing ribonucleolytic activity (e.g., as measured in an in vitro assay well known to those of skill in the art).

In other preferred embodiments, the modified human ribonuclease proteins (e.g., water-soluble polymer-RNase conjugates) of the present invention retain a significant portion of another desired property (e.g., other than ribonucleolytic activity (e.g., cancer cell killing capacity)). Although an understanding of the mechanism is not necessary to practice the present invention and the present invention is not limited to any particular mechanism of action, in some embodiments, a modified human ribonuclease protein (e.g., water-soluble polymer-RNase conjugate) is capable of killing target cells (e.g., cancer cells or microbially (e.g., virally) infected cells) in the absence of (e.g., less than 70%, less than 60%, less than 50%, less than 40%, less than 30%, less than 20%, less than 10%, or less than 5% of unmodified ribonuclease) ribonucleolytic activity (e.g., due to other characteristics of the human ribonuclease protein).

The present invention is not limited by the method utilized for conjugating a water-soluble polymer to a human ribonuclease of the present invention. Multiple types of chemistries are known in the art and may find use in the generation of the compositions of the present invention. These methods have been describe in detail (See, e.g., Zalipsky, Bioconjugate Chem 6, 150-165 (1995); Kinstler et al., Advanced Drug Delivery Reviews 54, 477-485 (2002); and Roberts et al., Advanced Drug Delivery Reviews 54, 459-476 (2002)). In some embodiments, the present invention utilizes a conjugation chemistry useful for conjugating an activated polymer of the present invention to a human ribonuclease.

For example, for obtaining N-terminally conjugated RNase (e.g., N-terminally PEGylated RNase), reductive alkylation may be used. A method for attaching without a linking group between the polymer (e.g., PEG) and the protein moiety is described in Francis et al., In: Stability of protein pharmaceuticals: in vivo pathways of degradation and strategies for protein stabilization (Eds. Ahern., T. and Manning, M. C.) Plenum, N.Y., 1991). In some embodiments, a method involving the use of N-hydroxy succinimidyl esters of carboxymethyl mPEG is used (See, e.g., U.S. Pat. No. 5,824,784, issued Oct. 20, 1998, hereby incorporated by reference in its entirety).

In some embodiments, the PEG-ribonuclease conjugate is purified after conjugation. The present invention is not limited by the type of purification process utilized. Indeed, a variety of processes may be utilized including, but not limited to, gel filtration chromatography, ion exchange chromatography, hydrophobic interaction chromatography, size exclusion chromatography, and other methods well known in the art.

For example, in some embodiments, a water-soluble polymer-RNase conjugate can be purified to obtain one or more different types of conjugates (e.g., a conjugate covalently bound to a single polymer). In some embodiments, the products of a conjugation reaction are purified to obtain (e.g., on average) anywhere from 1, 2, 3, 4, or more polymers (e.g., PEGs) per human ribonuclease. In some embodiments, gel filtration chromatography is used to separate/fractionate ribonucleases covalently attached to different numbers of polymers or to separate a conjugate from non-conjugated protein or from non-conjugated polymer. Gel filtration columns are well known in the art and available from multiple sources (e.g., SUPERDEX and SEPHADEX columns from Amersham Biosciences, Piscataway, N.J.).

In some embodiments, the present invention provides a composition comprising a water-soluble polymer-human ribonuclease conjugate. In some embodiments, the composition is administered to a patient in order to treat cancer. Thus, in some embodiments, the present invention provides a method of treating cancer comprising administering a composition comprising a water-soluble polymer-human ribonuclease conjugate.

In some embodiments, a therapeutic composition of the invention comprises an antibody and a ribonuclease. The antibody may provide cell or tissue specific targeting, and/or additional therapeutic benefits. The following table lists the mechanisms of some cancer therapeutic antibodies, including three antibody conjugates that carry a toxic payload for lymphomas and leukemias. (Drug Discovery Today, Vol. 8, No. 11 Jun. 2003). Two of the conjugates, ZEVALIN and BEXXAR, carry radioactive iodine as the toxin and the third, MYLOTARG, carries a cytotoxic antitumor antibiotic, calicheaminin which is isolated from a bacterial fermentation. The Mylotarg antibody binds specifically to the CD33 antigen which is expressed on the surface of leukemic blasts that are found in more than 80% of patients with acute myeloid leukemia (AML). The antibody in this conjugate has approximately 98.3% of its amino acid sequences derived from human origins.

TABLE 1

| Antibody Mode of Action | Product | Antibody Target |
| --- | --- | --- |
| Blockade Ligand binding | ERBITUX | EGF receptor |
| | HUMAX-EGFR | EGF receptor |
| Complement Dependent Cytotoxicity | RITUXAN | CD20 |
| | HUMAX-CD20 | CD20 |
| | CAMPATH-1H | CD52 |
| Antibody dependent cell-mediated cytotoxicity | RIXTUXAN | CD20 |
| | HUMAX-CD20 | CD20 |
| | HERCEPTIN | Her-2/neu |
| | HUMAX-EGFR | EGF receptor |
| Apoptosis induction | Various | IdiotypeB cell tumors |
| Disruption signaling | 2C4 (PERTUZUMAB) | Her-2/neu |
| Inhibition angiogenesis | AVASTIN | VEGF |
| Targeted radiolysis conjugate | ZEVALIN | CD20 |
| | BEXXAR | CD20 |
| Toxin-mediated killing by conjugate | MYLOTARG | CD33 |
| Antagonist activity | MDX-010 | CTLA4 |
| Agonist activity | Various | CD40, CD137 |
| Antagonist activity | Preclinical MAb | Epithelial cell receptor protein tyrosine kinase (EphA2) |
| Antagonist activity | Phase II Mab | alpha 5 beta 3 integrin (receptor) |
| Antagonist activity | Phase I bispecific single chain monoclonal antibody | CD19/CD3 |
| Antagonist activity | Preclinical MAb | Interleukin 9 |
| Antagonist activity | RespiGam Polyclonal Antibody | Respiratory syncytial virus |
| Antagonist activity | Phase II MAb | CD2 |
| Catalytic Activity | Mab | Cocaine cleavage |
| Anti-infective, bacteria | Mab | bacteria |
| Immunosuppressive Agents | Mab | Graft versus Host Disease |
| Anti-infective, virus | Mab | Human metapneumovirus |
| Cytostatic agent | Mab | Platelet derived growth factor |

TABLE 1-continued

| Antibody Mode of Action | Product | Antibody Target |
| --- | --- | --- |
| Cancer growth and metastosis | Preclinical MAb | Human beta hydroxylases |
| Treatment of autoimmune disease | MAb Medi 507 | Mixed lymphocyte responses |
| Anti-infective, virus | Polyclonal antibody | cytomegalovirus |
| Anti-idiotype antibody | Mab | Neu-glycolyl-GM3 ganglioside |
| Prodrug carrier | Mab | Immungen's CC 1065 prodrugs |
| Toxin-mediated killing by conjugate | Preclinical MAb and taxane derivatives | Various by Immunogen |
| Toxin-mediated killing by conjugate | Cantuzumab mertansine conjugate | Can Ag receptor by immunogen |
| Toxin-mediated killing by conjugate | Phase II MAb maytansinoid conjugate | CD56 |
| Toxin for mitosis inhibition | MAb maitansine conjugate | various |
| Toxin-mediated killing by conjugate | Preclinical MAb cytotoxic drug DM1 conjugate | Antigen on squamous cell cancer (Immunogen) |

Any of the targeting antibodies or agents used in these products may also be employed by the compositions and methods of the present invention.

Generally, the most specific method for targeting toxins is the use of monoclonal antibodies or antibody fragments that are designed to recognize surface antigens specific to tumor cells. Because normal cells lack the surface antigens, they are not targeted and killed by the toxin conjugate. Whole antibodies have two domains: a variable domain that gives the antibody its affinity and binding specificity and a constant domain that interacts with other portions of the immune system to stimulate immune responses in the host organism. The variable domain is composed of the complementarity determining regions (CDRs), which bind to the antibody's target, and a framework region that anchors the CDRs to the rest of the antibody and helps maintain CDR shape. The six CDR's in each antibody differ in length and sequence between different antibodies and are mainly responsible for the specificity (recognition) and affinity (binding) of the antibodies to their target markers.

In addition to antibody delivery vectors, toxic molecules can be delivered to cancer cells using several other specific and non-specific vectors including peptides, polymers, dendrimers, liposomes, polymeric nanoparticles, and block copolymer micelles. For example, peptides that bind to the leutinizing hormone-releasing hormone have been used to target a small molecule toxin, camptothecin, to ovarian cancer cells (Journal of Controlled Release, 2003, 91, 61-73).

Ribonucleases are effective toxins in human cells, particularly against cancer cells. The following references, each of which is herein incorporated by reference in its entirety, describe some chemical conjugates of ribonucleases to targeting proteins (including proteins and antibodies): Newton et al. (2001), Blood 97(2): 528-35, Hursey et al. (2002) Leuk Lymphoma 43(5): 953-9, Rybak et al., (1991) Journal of Biological Chemistry 266(31): 21202-7, Newton et al. (1992) Journal of Biological Chemistry 267(27): 19572-8, Jinno and Ueda (1996) Cancer Chemother Pharmacol 38: 303-308, Yamamura et al. (2002) Eur J Surg 168: 49-54, Jinno et al. (1996) Life Sci 58: 1901-1908, Suzuki et al. (1999) Nature Biotechnology 17(3): 265-70, Rybak et al. (1992) Cell Biophys 21(1-3): 121-38, Jinno et al. (2002) Anticancer Res. 22: 4141-4146.

In some embodiments, the present invention provides recombinant constructs comprising a nucleic acid sequence that encodes one or more the amino acid sequences described herein. In some embodiments of the present invention, the constructs comprise a vector, such as a plasmid or viral vector, into which a sequence of SEQ ID:NO 2, or related sequence, has been inserted, in a forward or reverse orientation. In still other embodiments, the heterologous structural sequence is assembled in appropriate phase with translation initiation and termination sequences.

In some embodiments of the present invention, the appropriate DNA sequence is inserted into the vector using any of a variety of procedures. In general, the DNA sequence is inserted into an appropriate restriction endonuclease site(s) by procedures known in the art. Large numbers of suitable vectors are known to those of skill in the art, and are commercially available. Such vectors include, but are not limited to, the following vectors: 1) Bacterial—pQE70, pQE60, pQE-9 (Qiagen), pET 22b, pET26b, pET 30b (Novagen brand, EMD Chemicals), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWL-NEO, pSV2CAT, pOG44, PXT1, pSG (Stratagene) pSVK3, pBPV, pMSG, pSVL (Pharmacia). Any other plasmid or vector may be used as long as they are replicable and viable in the host. In some embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the E. coli lac or trp, the phage lambda PL and PR, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline, kanamycin, or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin by 100 to 270, a cytomegalovirus early promoter enhancer, the polyoma enhancer on the late side of the replication origin, and adenovirus enhancers.

In other embodiments, the expression vector also contains a ribosome-binding site for translation initiation and a transcription terminator. In still other embodiments of the present invention, the vector may also include appropriate sequences for amplifying expression.

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomyces cerevisiae, Schizosaccharomyces pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, transformation, or electroporation. Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

An example of a suitable recombinant product method involves use of a plasmid conferring drug resistance such as ampicillin (e.g., pET22b) or kanamycin (e.g., pET-26b, pET-30b) and containing the gene coding for the ribonuclease protein. The plasmid harboring the gene is transformed into an *E. coli* cell line. Cells that can be used include, but are not limited to, *E. coli* B or K strain and the related mutant strains such as HB101, JM109, DHa5, BL-21A1 and BL21DE3. Expression of the ribonuclease protein can be induced during fermentation by addition of carbohydrates such as arabinose or lactose or their analogues including isopropyl-beta-D-thiogalactopyranoside (IPTG). The ribonuclease protein can be produced as a soluble product or in inclusion bodies. For soluble production, the protein is isolated and purified as below using column chromatography. For inclusion body production, the cells are mechanically, enzymatically or/and chemically lysed. The cell pellet containing the inclusion bodies is separated from the soluble material by multiple methods, including diafiltration or centrifugation. The inclusion bodies are solubilized with a denaturant such as urea or guanidine hydrochloride. Reducing agents, such as low molecular weight thiols (e.g., dithiothreitol) or tris(2-carboxyethyl)phosphine can be added. Addition of acid causes precipitate to form that can be removed from the solution by filtration and/or centrifugation.

The protein is folded by changing to a buffer that may include a variety of agents to assist in protein folding. Examples of such reagents include: arginine, polyethylene glycol, sulfobetaines, detergents, organic salts and/or chaotropes. The buffer is changed again for compatibility with the first column chromatography step and precipitate can be removed by filtration or centrifugation. The column steps include: anion exchange, cation exchange and hydrophobic interaction. Examples of anion exchange resins include but are not limited to: Q Sepharose XL, UNO Q-1, Poros 50 HQ, Toyopearl QAE 550c, Separon HemaBio 1000Q, Q-Cellthru Bigbeads Plus, Q Sepharose HP, Toyopearl SuperQ 650s, Macro-Prep 25Q, TSK-Gel Q-5PW-HR, Poros QE/M, Q Sepharose FF, Q HyperD 20, Q Zirconia, Source 30Q, Fractogel EMD TMAE 650s, and Express-Ion Q. Examples of cation exchange resins include but are not limited to: SP Sepharose XL, Poros 50 HS, Toyopearl SP 550c, SP Sepharose BB, Source 30S, TSKGel SP-5PW-HR20, Toyopearl SP 650c, Heparin Sepharose FF, SP Sepharose FF, CM Sepharose FF, Heparin Toyopearl 650m, SP Toyopearl 650m, CM Toyopearl 650m, Ceramic Heparin HyperD M, Ceramic S HyperD 20, and Ceramic CM HyperD F. Examples of hydrophobic interaction resins include but are not limited to: TSK-gel Phenyl-5PW, TSK-gel Ether-5PW, TSK-gel Butyl-NPR, Toyopearl Butyl-650S, Toyopearl Ether-650S, Toyopearl Phenyl-650S, Toyopearl Butyl-650M, Toyopearl Ether-650M, Toyopearl Phenyl-650M, Butyl-Sepharose 4 FF, Octyl-Sepharose 4 FF, Octyl-Sepharose CL-4B, and Phenyl-Sepharose 6 FF (high or low substitution). The final product is exchanged into a neutral buffer for long term storage.

In some embodiments, the compositions and methods of the present invention are used to treat diseased cells, tissues, organs, or pathological conditions and/or disease states in a subject organism (e.g., a mammalian subject including, but not limited to, humans and veterinary animals), or in in vitro and/or ex vivo cells, tissues, and organs. In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the RNases of the present invention target cancer stem cells.

In subjects who are determined to be at risk of having cancer, the compositions of the present invention are administered to the subject preferably under conditions effective to decrease angiogenesis, proliferation and/or induce killing (e.g., apoptosis) of cancer cells in the event that they develop.

The present invention further provides pharmaceutical compositions (e.g., comprising the cell killing compositions described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The preferred method of administration is by intravenous or IP injection. It is alternatively possible to use injection into the tumor to be treated. In some embodiments, administration is continued as an adjuvant treatment for an additional period (e.g., several days to several months).

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active pharmaceutical agents of the formulation.

In some preferred embodiments, a ribonuclease is co-administered with other medical interventions, either simultaneously or sequentially. For example, for cancer therapy, any oncolytic agent that is routinely used in a cancer therapy may be co-administered with the compositions and methods of the present invention. For example, the U.S. Food and Drug Administration maintains a formulary of oncolytic agents approved for use in the United States. International counterpart agencies to the U.S.F.D.A. maintain similar formularies. Table 2 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents. It is contemplated, that in some cases, co-administration with the compositions of the present invention permits lower doses of such compounds, thereby reducing toxicity.

TABLE 2

| | | |
|---|---|---|
| Aldesleukin (des-alanyl-1, serine-125 human interleukin-2) | PROLEUKIN | Chiron Corp., Emeryville, CA |
| Alemtuzumab (IgG1κ anti CD52 antibody) | CAMPATH | Millennium and ILEX Partners, LP, Cambridge, MA |
| Alitretinoin (9-cis-retinoic acid) | PANRETIN | Ligand Pharmaceuticals, Inc., San Diego CA |
| Allopurinol (1,5-dihydro-4H-pyrazolo[3,4-d]pyrimidin-4-one monosodium salt) | ZYLOPRIM | GlaxoSmithKline, Research Triangle Park, NC |
| Altretamine (N,N,N',N',N",N",-hexamethyl-1,3,5-triazine-2,4,6-triamine) | HEXALEN | US Bioscience, West Conshohocken, PA |
| Amifostine (ethanethiol, 2-[(3-aminopropyl)amino]-, dihydrogen phosphate (ester)) | ETHYOL | US Bioscience |
| Anastrozole (1,3-Benzenediacetonitrile,a,a,a',a'-tetramethyl-5-(1H-1,2,4-triazol-1-ylmethyl)) | ARIMIDEX | AstraZeneca Pharmaceuticals, LP, Wilmington, DE |
| Arsenic trioxide | TRISENOX | Cell Therapeutic, Inc., Seattle, WA |
| Asparaginase (L-asparagine amidohydrolase, type EC-2) | ELSPAR | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| Bevacizumab | AVASTIN | Genentech |
| bexarotene capsules (4-[1-(5,6,7,8-tetrahydro-3,5,5,8,8-pentamethyl-2-napthalenyl) ethenyl] benzoic acid) | TARGRETIN | Ligand Pharmaceuticals |
| bexarotene gel | TARGRETIN | Ligand Pharmaceuticals |
| Bleomycin (cytotoxic glycopeptide antibiotics produced by *Streptomyces verticillus*; bleomycin $A_2$ and bleomycin $B_2$) | BLENOXANE | Bristol-Myers Squibb Co., NY, NY |
| Capecitabine (5'-deoxy-5-fluoro-N-[(pentyloxy)carbonyl]-cytidine) | XELODA | Roche |
| Carboplatin (platinum, diammine [1,1-cyclobutanedicarboxylato(2-)-0,0']-, (SP-4-2)) | PARAPLATIN | Bristol-Myers Squibb |
| Carmustine (1,3-bis(2-chloroethyl)-1-nitrosourea) | BCNU, BICNU | Bristol-Myers Squibb |
| Carmustine with Polifeprosan 20 Implant | GLIADEL WAFER | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | CELEBREX | Searle Pharmaceuticals, England |
| Cetuximab | ERBITUX | ImClone/BMS |
| Chlorambucil (4-[bis(2chlorethyl)amino]benzenebutanoic acid) | LEUKERAN | GlaxoSmithKline |
| Cisplatin ($PtCl_2H_6N_2$) | PLATINOL | Bristol-Myers Squibb |
| Cladribine (2-chloro-2'-deoxy-b-D-adenosine) | LEUSTATIN, 2-CDA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | CYTOXAN, NEOSAR | Bristol-Myers Squibb |
| Cytarabine (1-b-D-Arabinofuranosylcytosine, $C_9H_{13}N_3O_5$) | CYTOSAR-U | Pharmacia & Upjohn Company |
| cytarabine liposomal | DEPOCYT | Skye Pharmaceuticals, Inc., San Diego, CA |
| Dacarbazine (5-(3,3-dimethyl-1-triazeno)-imidazole-4-carboxamide (DTIC)) | DTIC-DOME | Bayer AG, Leverkusen, Germany |
| Dactinomycin, actinomycin D (actinomycin produced by *Streptomyces parvullus*, $C_{62}H_{86}N_{12}O_{16}$) | COSMEGEN | Merck |

TABLE 2-continued

| | | |
|---|---|---|
| Darbepoetin alfa (recombinant peptide) | ARANESP | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DANUOXOME | Nexstar Pharmaceuticals, Inc., Boulder, CO |
| Daunorubicin HCl, daunomycin ((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | CERUBIDINE | Wyeth Ayerst, Madison, NJ |
| Denileukin diftitox (recombinant peptide) | ONTAK | Seragen, Inc., Hopkinton, MA |
| Dexrazoxane ((S)-4,4'-(1-methyl-1,2-ethanediyl)bis-2,6-piperazinedione) | ZINECARD | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | TAXOTERE | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | ADRIAMYCIN, RUBEX | Pharmacia & Upjohn Company |
| doxorubicin | ADRIAMYCIN PFS INTRAVENOUS INJECTION | Pharmacia & Upjohn Company |
| doxorubicin liposomal | DOXIL | Sequus Pharmaceuticals, Inc., Menlo park, CA |
| dromostanolone propionate (17b-Hydroxy-2a-methyl-5a-androstan-3-one propionate) | DROMOSTANOLONE | Eli Lilly & Company, Indianapolis, IN |
| Dromostanolone propionate | MASTERONE INJECTION | Syntex, Corp., Palo Alto, CA |
| Elliott's B Solution | ELLIOTT'S B SOLUTION | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | ELLENCE | Pharmacia & Upjohn Company |
| Epoetin alfa (recombinant peptide) | EPOGEN | Amgen, Inc |
| Erlotinib (N-(3-ethynylphenyl)-6,7-bis(2-methoxyethoxy)quinazolin-4-amine) | TARCEVA | Genentech/OSI |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | EMCYT | Pharmacia & Upjohn Company |
| Etoposide phosphate (4'-Demethyl-epipodophyllotoxin 9-[4,6-O-(R)-ethylidene-(beta)-D-glucopyranoside], 4'-(dihydrogen phosphate)) | ETOPOPHOS | Bristol-Myers Squibb |
| etoposide, VP-16 (4'-demethyl-epipodophyllotoxin 9-[4,6-0-(R)-ethylidene-(beta)-D-glucopyranoside]) | VEPESID | Bristol-Myers Squibb |
| Exemestane (6-methylenandrosta-1,4-diene-3,17-dione) | AROMASIN | Pharmacia & Upjohn Company |
| Filgrastim (r-metHuG-CSF) | NEUPOGEN | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | FLUDARA | Berlex Laboratories, Inc., Cedar Knolls, NJ |
| Fluorouracil, 5-FU (5-fluoro-2,4(1H,3H)-pyrimidinedione) | ADRUCIL | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | FASLODEX | IPR Pharmaceuticals, Guayama, Puerto Rico |
| Gefitinib (N-(3-chloro-4-fluoro-phenyl)-7-methoxy-6-(3-morpholin-4-ylpropoxy)quinazolin-4-amine) | IRESSA | AstraZeneca |
| Gemcitabine (2'-deoxy-2',2'-difluorocytidine monohydrochloride (b-isomer)) | GEMZAR | Eli Lilly |
| Gemtuzumab Ozogamicin (anti-CD33 hP67.6) | MYLOTARG | Wyeth Ayerst |

TABLE 2-continued

| | | |
|---|---|---|
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•($C_2H_4O_2$)$_x$ | ZOLADEX IMPLANT | AstraZeneca Pharmaceuticals |
| Hydroxyurea | HYDREA | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | ZEVALIN | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | IDAMYCIN | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | GLEEVEC | Novartis AG, Basel, Switzerland |
| Interferon alfa-2a (recombinant peptide) | ROFERON-A | Hoffmann-La Roche, Inc., Nutley, NJ |
| Interferon alfa-2b (recombinant peptide) | INTRON A (LYOPHILIZED BETASERON) | Schering AG, Berlin, Germany |
| Irinotecan HCl ((4S)-4,11-diethyl-4-hydroxy-9-[(4-piperi-dinopiperidino)carbonyloxy]-1H-pyrano[3',4': 6,7] indolizino[1,2-b] quinoline-3,14(4H,12H) dione hydrochloride trihydrate) | CAMPTOSAR | Pharmacia & Upjohn Company |
| Letrozole (4,4'-(1H-1,2,4-Triazol-1-ylmethylene) dibenzonitrile) | FEMARA | Novartis |
| Leucovorin (L-Glutamic acid, N[4[[(2amino-5-formyl-1,4,5,6,7,8 hexahydro4oxo-6-pteridinyl)methyl]amino]benzoyl], calcium salt (1:1)) | WELLCOVORIN, LEUCOVORIN | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S$•HCl) | ERGAMISOL | Janssen Research Foundation, Titusville, NJ |
| Lomustine (1-(2-chloro-ethyl)-3-cyclohexyl-1-nitrosourea) | CEENU | Bristol-Myers Squibb |
| Meclorethamine, nitrogen mustard (2-chloro-N-(2-chloroethyl)-N-methylethanamine hydrochloride) | MUSTARGEN | Merck |
| Megestrol acetate 17α(acetyloxy)-6-methylpregna-4,6-diene-3,20-dione | MEGACE | Bristol-Myers Squibb |
| Melphalan, L-PAM (4-[bis(2-chloroethyl) amino]-L-phenylalanine) | ALKERAN | GlaxoSmithKline |
| Mercaptopurine, 6-MP (1,7-dihydro-6H-purine-6-thione monohydrate) | PURINETHOL | GlaxoSmithKline |
| Mesna (sodium 2-mercaptoethane sulfonate) | MESNEX | Asta Medica |
| Methotrexate (N-[4-[[(2,4-diamino-6-pteridinyl)methyl]methylamino]benzoyl]-L-glutamic acid) | METHOTREXATE | Lederle Laboratories |
| Methoxsalen (9-methoxy-7H-furo[3,2-g][1]-benzopyran-7-one) | UVADEX | Therakos, Inc., Way Exton, Pa |
| Mitomycin C | MUTAMYCIN | Bristol-Myers Squibb |
| mitomycin C | MITOZYTREX | SuperGen, Inc., Dublin, CA |
| Mitotane (1,1-dichloro-2-(o-chlorophenyl)-2-(p-chlorophenyl) ethane) | LYSODREN | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | NOVANTRONE | Immunex Corporation |
| Nandrolone phenpropionate | DURABOLIN-50 | Organon, Inc., West Orange, NJ |
| Nofetumomab | VERLUMA | Boehringer Ingelheim Pharma KG, Germany |
| Oprelvekin (IL-11) | NEUMEGA | Genetics Institute, Inc., Alexandria, VA |
| Oxaliplatin (cis-[(1R,2R)-1,2-cyclohexanediamine-N,N'] [oxalato(2-)-O,O'] platinum) | ELOXATIN | Sanofi Synthelabo, Inc., NY, NY |

TABLE 2-continued

| | | |
|---|---|---|
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | AREDIA | Novartis |
| Pegademase ((monomethoxypolyethylene glycol succinimidyl) 11-17-adenosine deaminase) | ADAGEN (PEGADEMASE BOVINE) | Enzon Pharmaceuticals, Inc., Bridgewater, NJ |
| Pegaspargase (monomethoxypolyethylene glycol succinimidyl L-asparaginase) | ONCASPAR | Enzon |
| Pegfilgrastim (covalent conjugate of recombinant methionyl human G-CSF (Filgrastim) and monomethoxypolyethylene glycol) | NEULASTA | Amgen, Inc |
| Pentostatin | NIPENT | Parke-Davis Pharmaceutical Co., Rockville, MD |
| Pipobroman | VERCYTE | Abbott Laboratories, Abbott Park, IL |
| Plicamycin, Mithramycin (antibiotic produced by *Streptomyces plicatus*) | MITHRACIN | Pfizer, Inc., NY, NY |
| Porfimer sodium | PHOTOFRIN | QLT Phototherapeutics, Inc., Vancouver, Canada |
| Procarbazine (N-isopropyl-μ-(2-methylhydrazino)-p-toluamide monohydrochloride) | MATULANE | Sigma Tau Pharmaceuticals, Inc., Gaithersburg, MD |
| Quinacrine (6-chloro-9-(1-methyl-4-diethyl-amine) butylamino-2-methoxyacridine) | ATABRINE | Abbott Labs |
| Rasburicase (recombinant peptide) | ELITEK | Sanofi-Synthelabo, Inc., |
| Rituximab (recombinant anti-CD20 antibody) | RITUXAN | Genentech, Inc., South San Francisco, CA |
| Sargramostim (recombinant peptide) | PROKINE | Immunex Corp |
| Sorafenib | NEXAVAR | Bayer/Onyx |
| Streptozocin (streptozocin 2-deoxy-2-[[(methylnitrosoamino)carbonyl]amino]-a(and b)-D-glucopyranose and 220 mg citric acid anhydrous) | ZANOSAR | Pharmacia & Upjohn Company |
| Sunitinib malate | SUTENT | Pfizer |
| Talc ($Mg_3Si_4O_{10}(OH)_2$) | SCLEROSOL | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | NOLVADEX | AstraZeneca Pharmaceuticals |
| Temozolomide (3,4-dihydro-3-methyl-4-oxoimidazo[5,1-d]-as-tetrazine-8-carboxamide) | TEMODAR | Schering |
| teniposide, VM-26 (4'-demethyl-epipodophyllotoxin 9-[4,6-0-(R)-2-thenylidene-(beta)-D-glucopyranoside]) | VUMON | Bristol-Myers Squibb |
| Testolactone (13-hydroxy-3-oxo-13,17-secoandrosta-1,4-dien-17-oic acid [dgr]-lactone) | TESLAC | Bristol-Myers Squibb |
| Thioguanine, 6-TG (2-amino-1,7-dihydro-6H-purine-6-thione) | THIOGUANINE | GlaxoSmithKline |
| Thiotepa (Aziridine,1,1',1"-phosphinothioylidynetris-, or Tris (1-aziridinyl) phosphine sulfide) | THIOPLEX | Immunex Corporation |
| Topotecan HCl ((S)-10-[(dimethylamino)methyl]-4-ethyl-4,9-dihydroxy-1H-pyrano[3',4': 6,7] indolizino [1,2-b] quinoline-3,14-(4H,12H)-dione monohydrochloride) | HYCAMTIN | GlaxoSmithKline |
| Toremifene (2-(p-[(Z)-4-chloro-1,2-diphenyl-1-butenyl]-phenoxy)-N,N-dimethylethylamine citrate (1:1)) | FARESTON | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | BEXXAR | Corixa Corp., Seattle, WA |
| Trastuzumab (recombinant monoclonal $IgG_1$ kappa anti-HER2 antibody) | HERCEPTIN | Genentech, Inc |

TABLE 2-continued

| | | |
|---|---|---|
| Tretinoin, ATRA (all-trans retinoic acid) | VESANOID | Roche |
| Uracil Mustard | URACIL MUSTARD CAPSULES | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | VALSTAR | Anthra --> Medeva |
| Vinblastine, Leurocristine ($C_{46}H_{56}N_4O_{10} \cdot H_2SO_4$) | VELBAN | Eli Lilly |
| Vincristine ($C_{46}H_{56}N_4O_{10} \cdot H_2SO_4$) | ONCOVIN | Eli Lilly |
| Vinorelbine (3',4'-didehydro-4'-deoxy-C'-norvincaleukoblastine [R-(R*,R*)-2,3-dihydroxybutanedioate (1:2)(salt)]) | NAVELBINE | GlaxoSmithKline |
| Zoledronate, Zoledronic acid ((1-Hydroxy-2-imidazol-1-yl-phosphonoethyl) phosphonic acid monohydrate) | ZOMETA | Novartis |

In some embodiments, the RNase of the present invention or a variant thereof is delivered to a target cell using complementation. For example, in some embodiments, two or more fragments of RNase are delivered separately to a cell. The fragments re-associate to form a functional enzyme. In some embodiments, two protein fragments are delivered. In other embodiments, vectors comprising nucleic acids encoding fragments of RNase are introduced into a cell or organism separately.

Suitable fragments for delivery by complementation may be determined by screening fragments (e.g., in a cell culture assay) for activity. Preferred fragments are those that rapidly re-associate to form a functional enzyme. Enzyme activity can be determined using any suitable method, including, but not limited to, those disclosed herein.

In some embodiments, the present invention utilizes digestion of RNases to produce S-peptide and S-protein (See, e.g., Hamachi et al., Bioorg Med Chem Lett 9, 1215-1218 (1999); Goldberg and Baldwin, Proc Natl Acad Sci, 96, 2019-2024 (1999); Asai et al., J Immun Meth, 299, 63-76 (2005); Backer et al., J Cont Release, 89, 499-511 (2003); Backer et al., Bioconj Chem, 15, 1021-1029 (2004)). For example, digestion of bovine RNase A by subtilisin results primarily in two fragments due to cleavage between Ala20 and Ser21. The shorter fragment (amino acids 1-20) is referred to as S-peptide, whereas the longer fragment (amino acids 20-124) is referred to as S-protein. The two fragments bind tightly at neutral pH and are sometime referred to as RNase S or RNase S'. RNase S is an active ribonuclease. The S-peptide-5-protein interaction has been used for affinity purification as well as in tertiary docking systems to target imaging agents or drugs. Thus, in some embodiments, the present invention provides S-peptide-S-protein for human ribonucleases.

In some embodiments, the RNase of the present invention or a variant thereof is provided as a nucleic acid encoding the RNase. Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual pharmaceutical compositions, and can generally be estimated based on $EC_{50}$s found to be effective in in vitro and in vivo animal models or based on the examples described herein. In general, dosage is from 0.01 μg to 100 g per kg of body weight, for example between 0.1 and 1000 mg per kg of body weight, preferably between 0.1 and 500 mg/kg of body weight, and still more preferably between 0.1 and 200 mg/kg of body weight (e.g., between 1 and 100 mg/kg), for a period of between 1 and 240 minutes (e.g., between 2 and 60 minutes and preferably between 15 and 45 minutes). Dosages may be administered as often as need to obtain the desired effect (e.g., reduction of tumor size or number of cancerous cells), for example once or more daily to once or more weekly or monthly. In some embodiments, the compositions are administered weekly at a dose of between 0.1 and 10 mg (e.g., 1 mg) for a period of between 5 and 60 minutes (e.g., 30 minutes). The treating physician can estimate repetition rates for dosing based on measured residence times and concentrations of the drug in bodily fluids or tissues. Following successful treatment, it may be desirable to have the subject undergo maintenance therapy to prevent the recurrence of the disease state once or more daily, to once every 20 years. In some preferred embodiments, dosages are 0.25-1000 mg/kg daily, weekly, or monthly to achieve the desired therapeutic effect. In some preferred embodiments, dosages are 50 mcg/m$^2$ to 400 mcg/m$^2$ daily, weekly, or monthly to achieve the desired therapeutic effect. Drugs are also sometimes dosed in units of activity per dose as opposed to amount (weight) of drug.

All publications, patents, patent applications and sequences identified by accession numbers mentioned in the above specification are herein incorporated by reference in their entirety. Although the invention has been described in connection with specific embodiments, it should be understood that the invention as claimed should not be unduly limited to such specific embodiments. Modifications and variations of the described compositions and methods of the invention that do not significantly change the functional features of the compositions and methods described herein are intended to be within the scope of the following claims.

We claim:

1. A composition comprising a nucleic acid sequence encoding a ribonuclease having
   i) a human RNase 1 amino acid sequence with at least 95% sequence identity to SEQ ID NO:1,
   ii) a cysteine at the position corresponding to position 4 of SEQ ID NO:1,
   iii) an arginine at the position corresponding to position 38 of SEQ ID NO:1,
   iv) a glycine at the position corresponding to position 39 of SEQ ID NO:1,
   v) an arginine at the position corresponding to position 67 of SEQ ID NO:1,
   vi) an arginine at the position corresponding to position 89 of SEQ ID NO:1,
   vii) an arginine at the position corresponding to position 90 of SEQ ID NO:1, and
   viii) a cysteine at the position corresponding to position 118 of SEQ ID NO:1.

2. The composition of claim 1, wherein said nucleic acid sequence comprises the nucleotide sequence of SEQ ID NO:2.

3. A method of introducing a recombinant construct into a host cell comprising:
   a) providing:
      i) a recombinant construct comprising the nucleic acid sequence of claim 1 encoding said ribonuclease, and
      ii) a host cell; and
   b) contacting said host cell with said recombinant construct such that said ribonuclease is expressed in said host cell.

4. The method of claim 3, wherein said recombinant construct comprises an expression vector.

5. The method of claim 3, wherein said recombinant construct comprises a virus.

6. The method of claim 3, wherein said recombinant construct comprises an adenovirus or adeno-associated virus.

7. The method of claim 3, wherein said host cell is located in vitro.

8. The method of claim 3, wherein said host cell is located in vivo.

9. The method of claim 3, wherein said host cell is prokaryotic.

10. The method of claim 3, wherein said host cell is eukaryotic.

* * * * *

SEQUENCE LISTING

```
<160> NUMBER OF SEQ ID NOS: 4

<210> SEQ ID NO 1
<211> LENGTH: 128
<212> TYPE: PRT
<213> ORGANISM: Artificial Sequence
<220> FEATURE:
<223> OTHER INFORMATION: Synthetic

<400> SEQUENCE: 1

Lys Glu Ser Cys Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30

Arg Asn Met Thr Gln Arg Gly Cys Lys Pro Val Asn Thr Phe Val His
        35                  40                  45

Glu Pro Leu Val Asp Val Gln Asn Val Cys Phe Gln Glu Lys Val Thr
    50                  55                  60

Cys Lys Arg Gly Gln Gly Asn Cys Tyr Lys Ser Asn Ser Ser Met His
65                  70                  75                  80

Ile Thr Asp Cys Arg Leu Thr Asn Arg Arg Tyr Pro Asn Cys Ala
                85                  90                  95

Tyr Arg Thr Ser Pro Lys Glu Arg His Ile Ile Val Ala Cys Glu Gly
                100                 105                 110

Ser Pro Tyr Val Pro Cys His Phe Asp Ala Ser Val Glu Asp Ser Thr
            115                 120                 125

<210> SEQ ID NO 2
<211> LENGTH: 384
<212> TYPE: DNA
<213> ORGANISM: Artificial Sequence
<220> FEATURE:
<223> OTHER INFORMATION: Synthetic

<400> SEQUENCE: 2
aaagaatctt gcgctaaaaa attccagcgt cagcacatgg actctgactc ttctccgtct     60
tcttcttcta cttactgcaa ccagatgatg cgtcgccgta acatgactca gcgtggttgc    120
aaaccggtta acactttcgt tcatgaaccg ctggttgact tcagaacgt ttgcttccag     180 gaaaaagtta cttgcaaacg cggtcagggt aactgctaca atctaactc ttctatgcat     240 atcactgact gccgtctgac gaatcgtcgc cgttacccga actgcgctta ccgtacttct    300
ccgaaagaac gtcatatcat cgttgcttgc gaaggttctc cgtacgttcc gtgtcatttc    360
gacgcttctg ttgaagactc tacc                                           384
```

```
<210> SEQ ID NO 3
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n is a, c, g, or t

<400> SEQUENCE: 3
ttgnttaact ttaagaagga gatatacata tg                              32

<210> SEQ ID NO 4
<211> LENGTH: 129
<212> TYPE: PRT
<213> ORGANISM: Artificial Sequence
<220> FEATURE:
<223> OTHER INFORMATION: Synthetic

<400> SEQUENCE: 4

Met Lys Glu Ser Cys Ala Lys Lys Phe Gln Arg Gln His Met Asp Ser
1               5                   10                  15

Asp Ser Ser Pro Ser Ser Ser Thr Tyr Cys Asn Gln Met Met Arg
            20                  25                  30

Arg Arg Asn Met Thr Gln Arg Gly Cys Lys Pro Val Asn Thr Phe Val
            35                  40                  45

His Glu Pro Leu Val Asp Val Gln Asn Val Cys Phe Gln Glu Lys Val
            50                  55                  60

Thr Cys Lys Arg Gly Gln Gly Asn Cys Tyr Lys Ser Asn Ser Ser Met
65                  70                  75                  80

His Ile Thr Asp Cys Arg Leu Thr Asn Arg Arg Arg Tyr Pro Asn Cys
                85                  90                  95

Ala Tyr Arg Thr Ser Pro Lys Glu Arg His Ile Ile Val Ala Cys Glu
            100                 105                 110

Gly Ser Pro Tyr Val Pro Cys His Phe Asp Ala Ser Val Glu Asp Ser
            115                 120                 125

Thr
```